(12) United States Patent
Renzi et al.

(10) Patent No.: US 7,452,507 B2
(45) Date of Patent: Nov. 18, 2008

(54) PORTABLE APPARATUS FOR SEPARATING SAMPLE AND DETECTING TARGET ANALYTES

(75) Inventors: Ronald F. Renzi, Tracy, CA (US); Karl Wally, Lafayette, CA (US); Robert W. Crocker, Fremont, CA (US); James F. Stamps, Livermore, CA (US); Stewart K. Griffiths, Livermore, CA (US); Julia A. Fruetel, Livermore, CA (US); Brent A. Horn, Roy, UT (US); Isaac R. Shokair, Livermore, CA (US); Daniel D. Yee, Dublin, CA (US); Victoria A. VanderNoot, Pleasanton, CA (US); Boyd J. Wiedenman, Aiken, SC (US); Jason A. A. West, Pleasanton, CA (US); Scott M. Ferko, Livermore, CA (US)

(73) Assignee: Sandia Corporation, Livermore, CA (US)

( * ) Notice: Subject to any disclaimer, the term of this patent is extended or adjusted under 35 U.S.C. 154(b) by 688 days.

(21) Appl. No.: 10/633,871

(22) Filed: Aug. 4, 2003

(65) Prior Publication Data

US 2004/0126279 A1    Jul. 1, 2004

Related U.S. Application Data

(60) Provisional application No. 60/400,884, filed on Aug. 2, 2002.

(51) Int. Cl.
*G01N 21/64* (2006.01)
*B01D 59/42* (2006.01)
*G01N 21/76* (2006.01)

(52) U.S. Cl. .............. 422/82.05; 422/82.08; 422/82.09; 422/100; 422/70; 204/452; 204/603

(58) Field of Classification Search .............. 422/82.05, 422/82.08, 82.09, 100; 204/603, 452
See application file for complete search history.

(56) References Cited

U.S. PATENT DOCUMENTS 4,695,430 A * 9/1987 Coville et al. ................ 422/65

(Continued)

FOREIGN PATENT DOCUMENTS

WO    WO 00/65337 A1    11/2000

OTHER PUBLICATIONS

Thomas, G.A., et al., "μChemLabTM—an integrated microanalytical system for chemical analysis using parallel gas and liquid phase microseparations", *Proc. SPIE*, vol. 3713, pp. 66-76, Unattended Ground Sensor Technologies and Applications, Edward M. Carapezza; David B. Law; K. Terry Stalker; Eds., Jul. 1999.

*Primary Examiner*—Jill Warden
*Assistant Examiner*—Paul S Hyun
(74) *Attorney, Agent, or Firm*—Dorsey & Whitney LLP

(57) ABSTRACT

Portable devices and methods for determining the presence of a target analyte using a portable device are provided. The portable device is preferably hand-held. A sample is injected to the portable device. A microfluidic separation is performed within the portable device and at least one separated component detected by a detection module within the portable device, in embodiments of the invention. A target analyte is identified, based on the separated component, and the presence of the target analyte is indicated on an output interface of the portable device, in accordance with embodiments of the invention.

21 Claims, 13 Drawing Sheets

U.S. PATENT DOCUMENTS

| | | | | |
|---|---|---|---|---|
| 5,043,590 | A * | 8/1991 | Strandberg et al. | 250/559.01 |
| 5,800,690 | A | 9/1998 | Chow et al. | |
| 6,126,804 | A | 10/2000 | Andresen | |
| 6,270,641 | B1 | 8/2001 | Griffiths et al. | |
| 6,290,909 | B1 | 9/2001 | Paul et al. | |
| 6,369,893 | B1 | 4/2002 | Christel et al. | |
| 6,398,956 | B1 * | 6/2002 | Coville et al. | 210/321.75 |
| 6,440,725 | B1 | 8/2002 | Pourahmadi et al. | |
| 6,446,516 | B1 * | 9/2002 | Sullivan | 73/864.81 |
| 6,475,364 | B1 | 11/2002 | Dubrow et al. | |
| 6,498,497 | B1 | 12/2002 | Chow et al. | |
| 6,627,076 | B2 | 9/2003 | Griffiths | |
| 6,733,730 | B1 | 5/2004 | Griffiths et al. | |
| 6,811,668 | B1 * | 11/2004 | Berndt et al. | 204/601 |
| 2001/0008212 | A1 | 7/2001 | Shepodd | |
| 2001/0052460 | A1 * | 12/2001 | Chien et al. | 204/450 |
| 2002/0071788 | A1 * | 6/2002 | Fujii et al. | 422/102 |
| 2003/0127610 | A1 | 7/2003 | Gallagher | |

\* cited by examiner

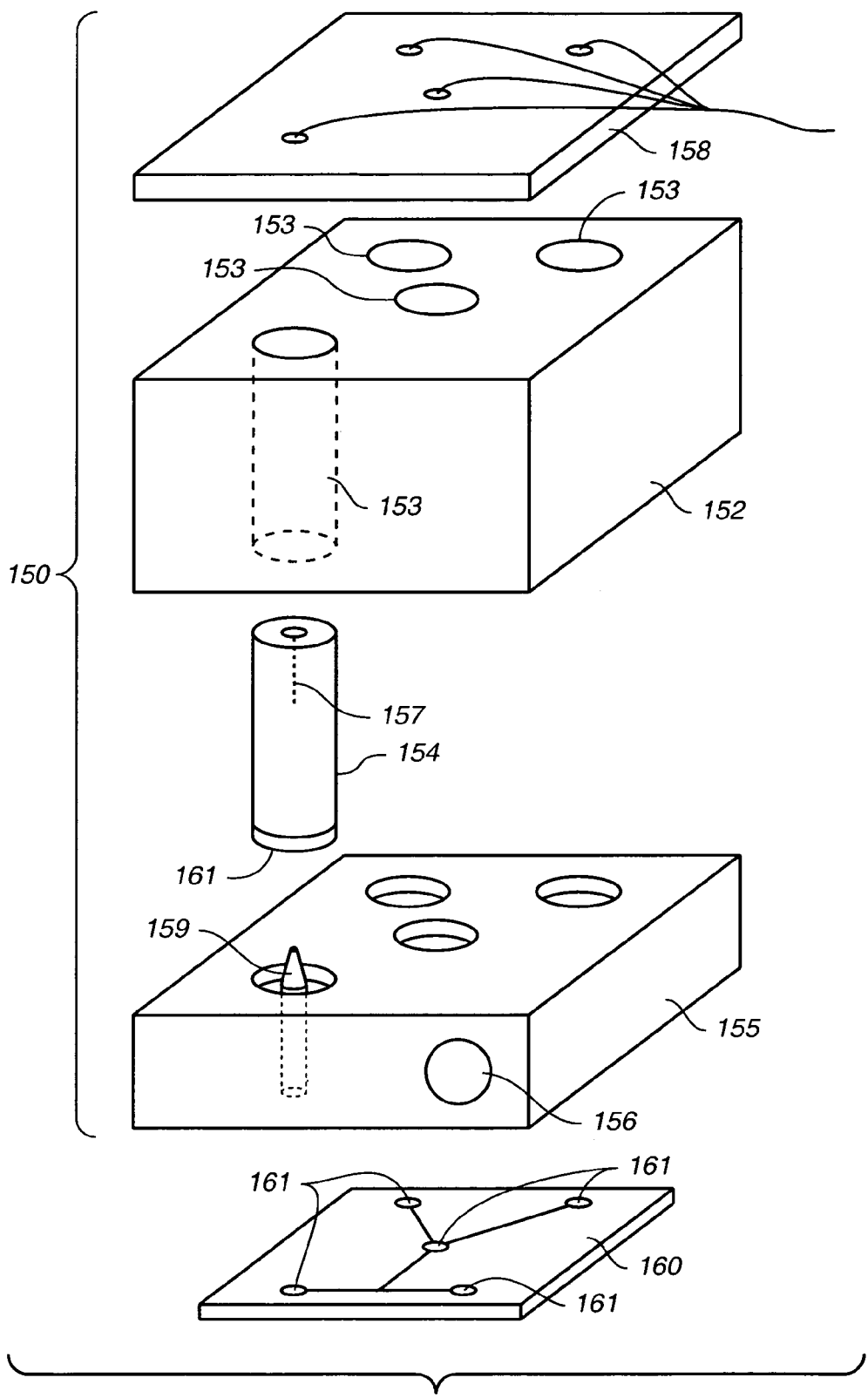
FIG._1

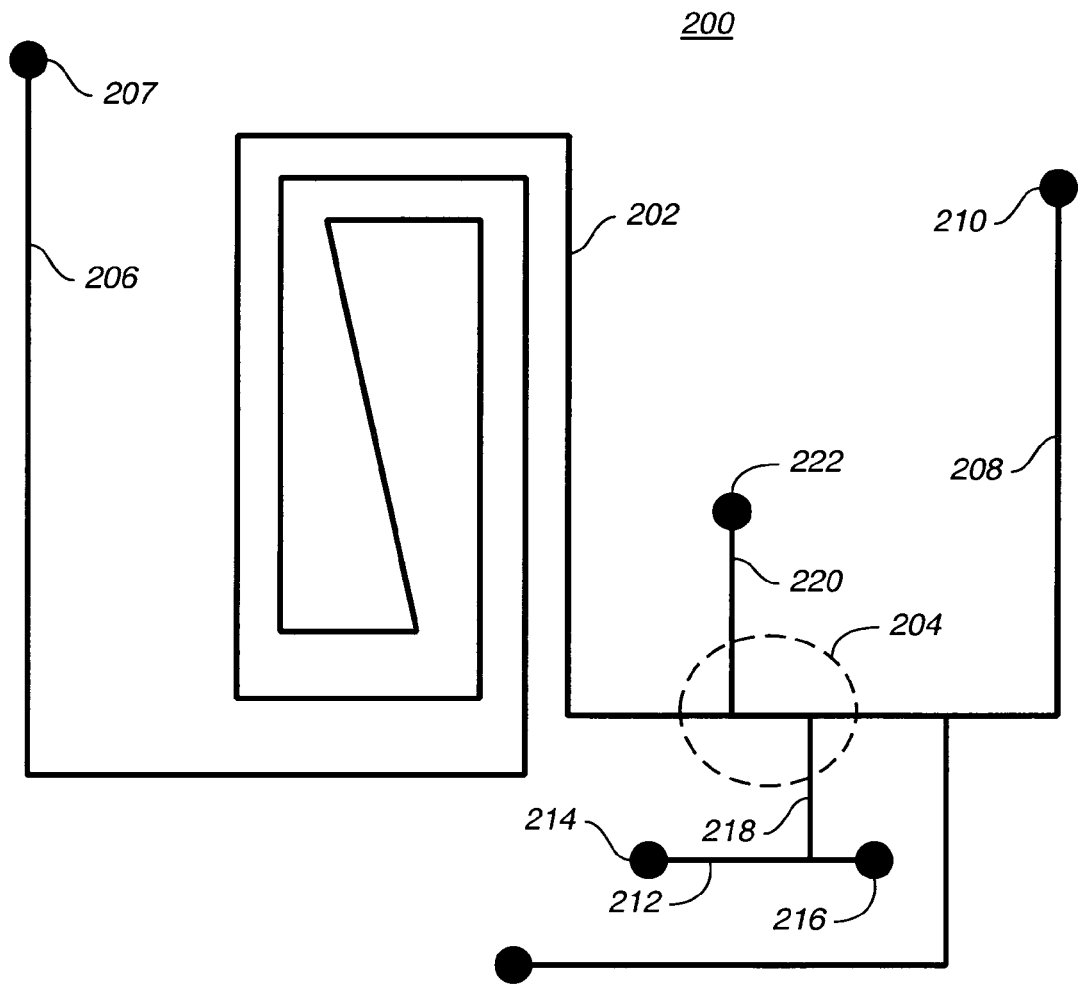
FIG._2

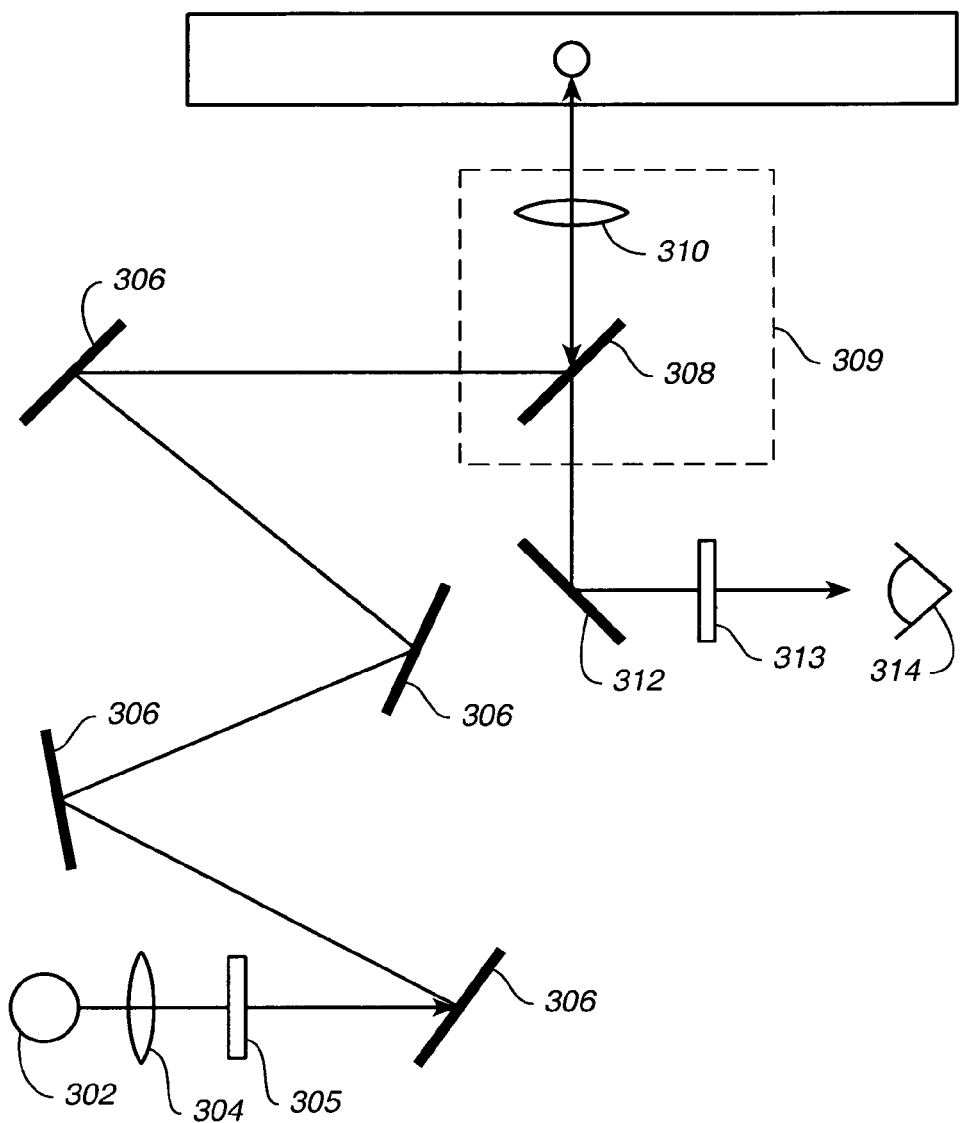
FIG._3

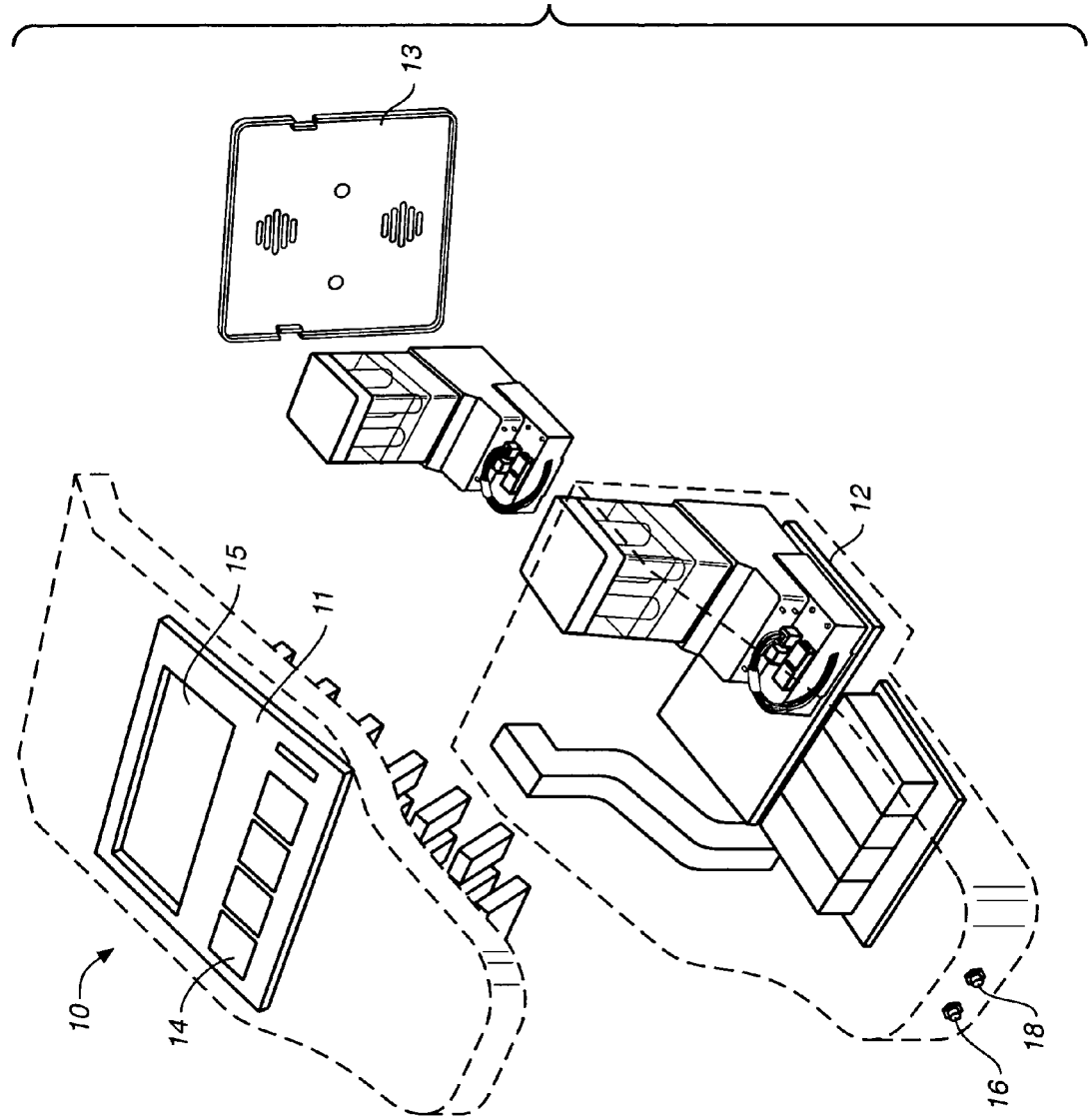
FIG._4

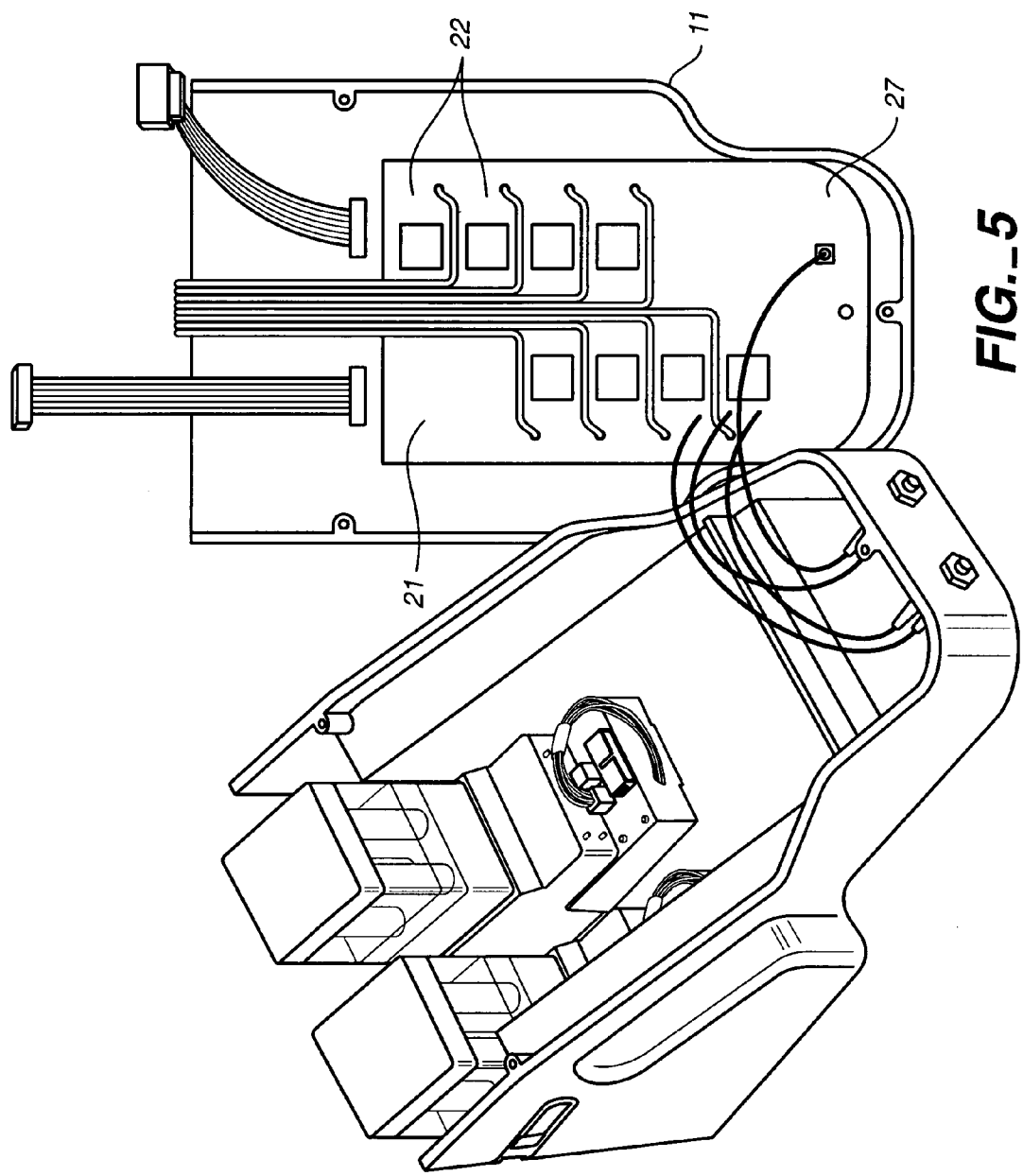
FIG._5

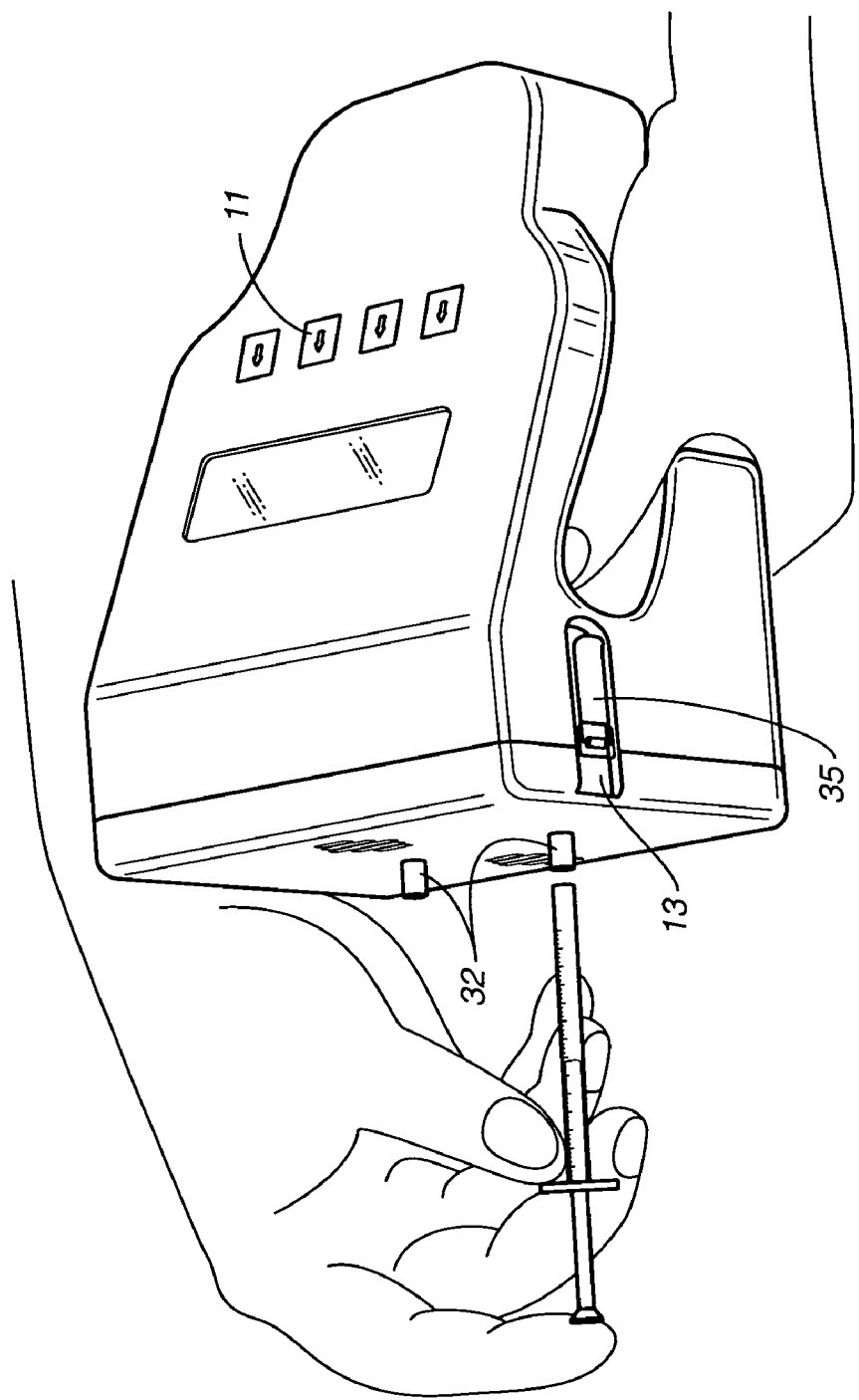
FIG._6

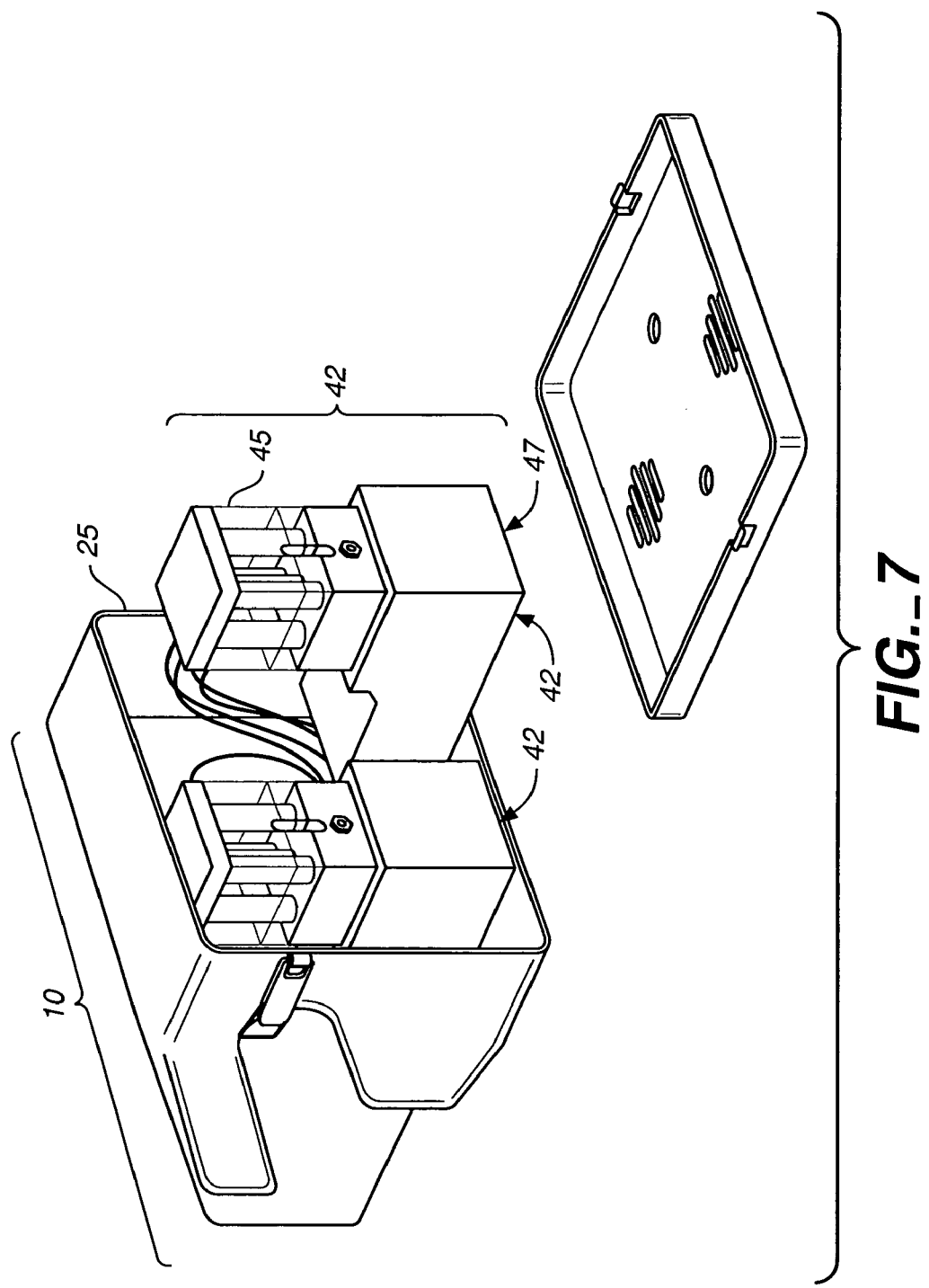
FIG._7

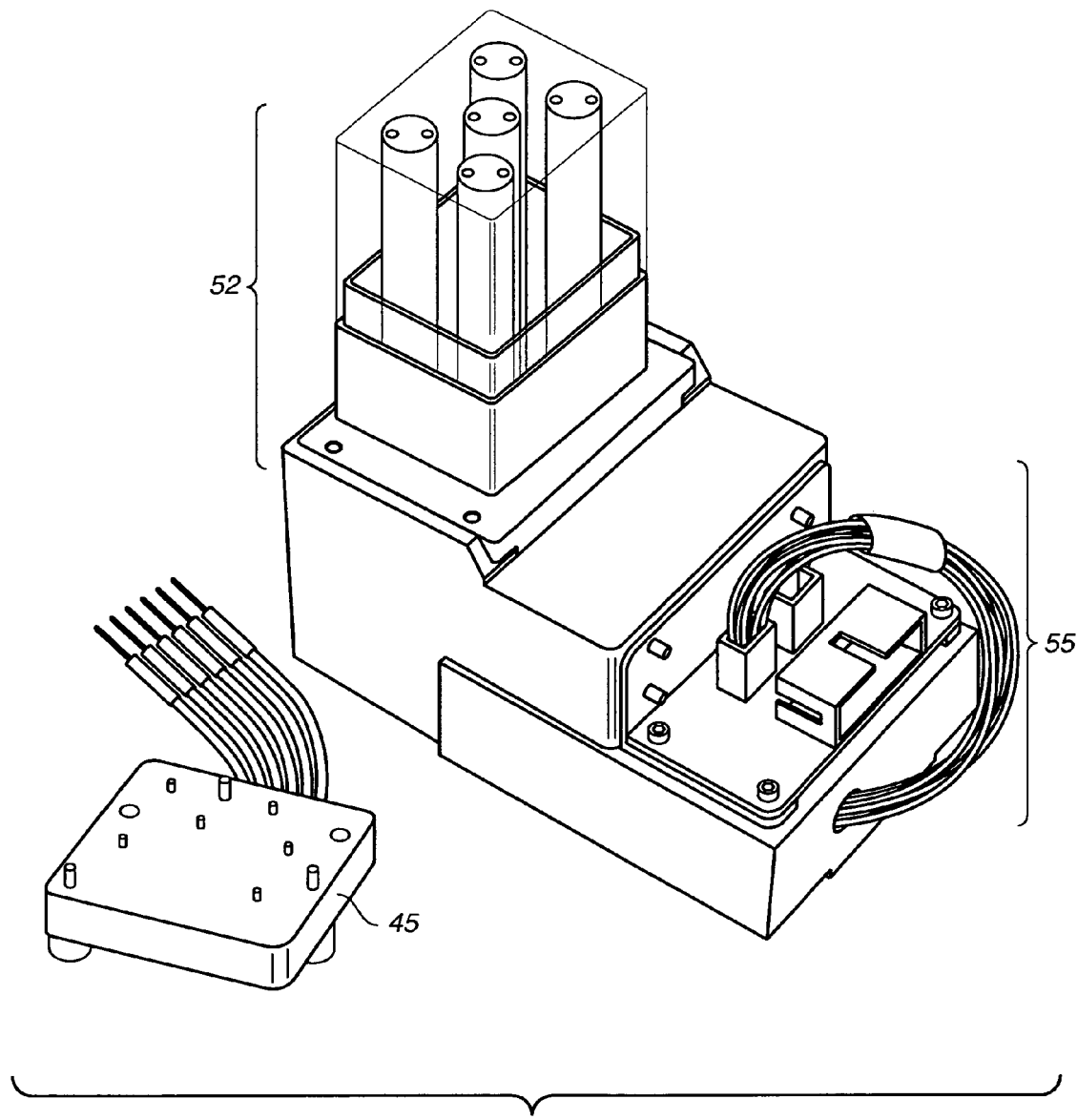
FIG._8

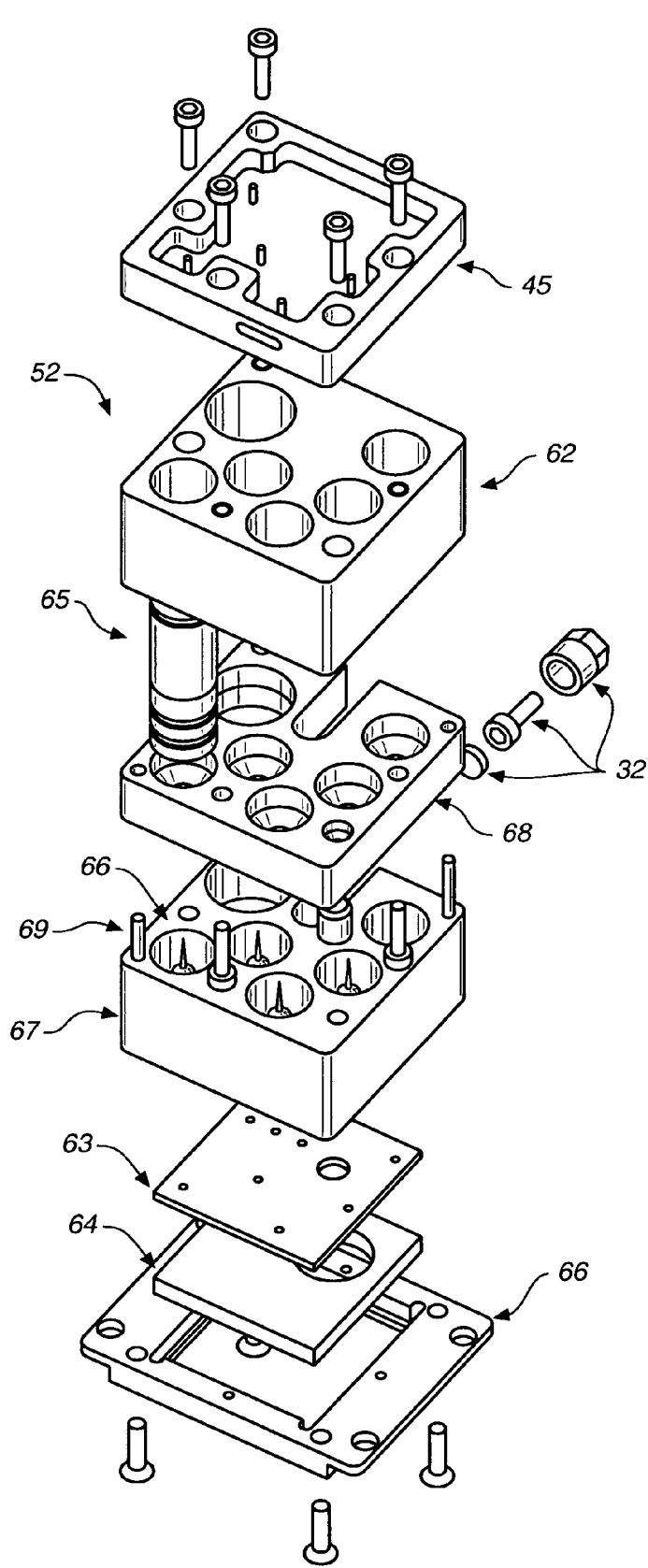
FIG._9

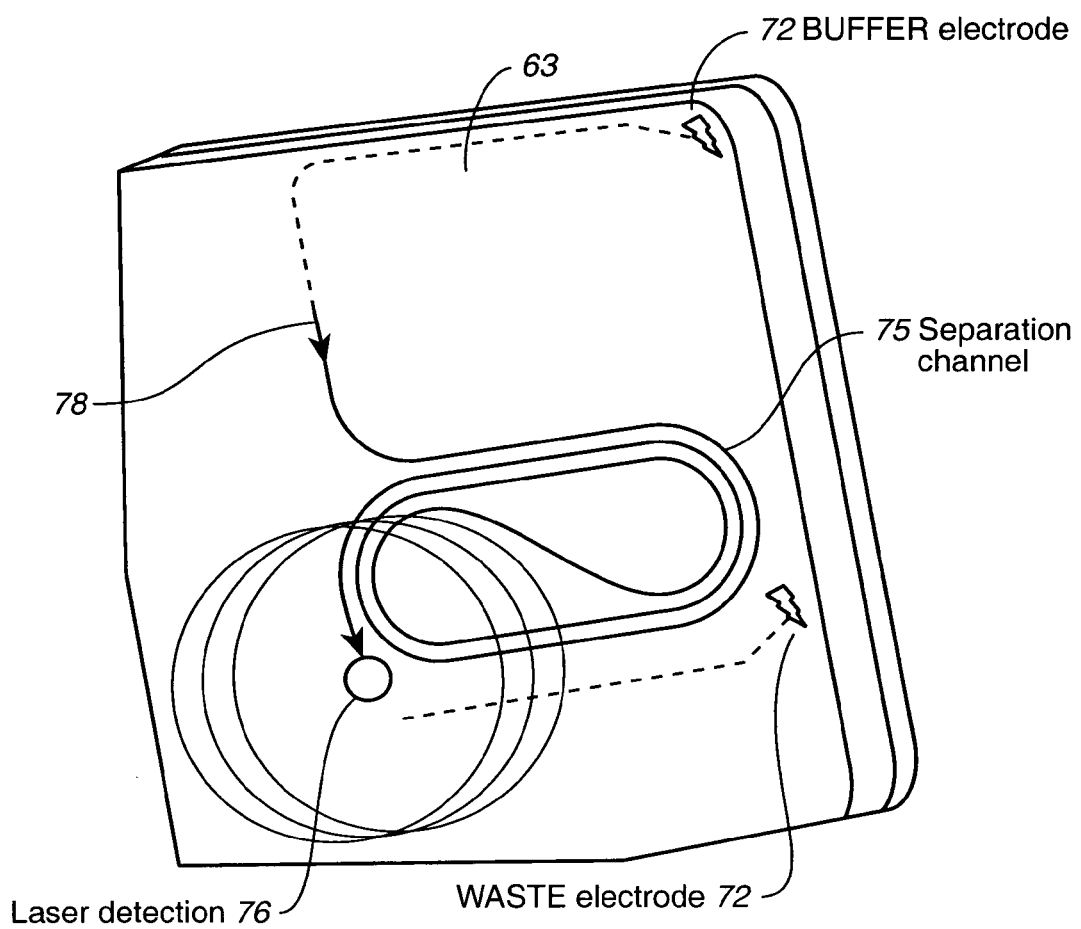
FIG._10

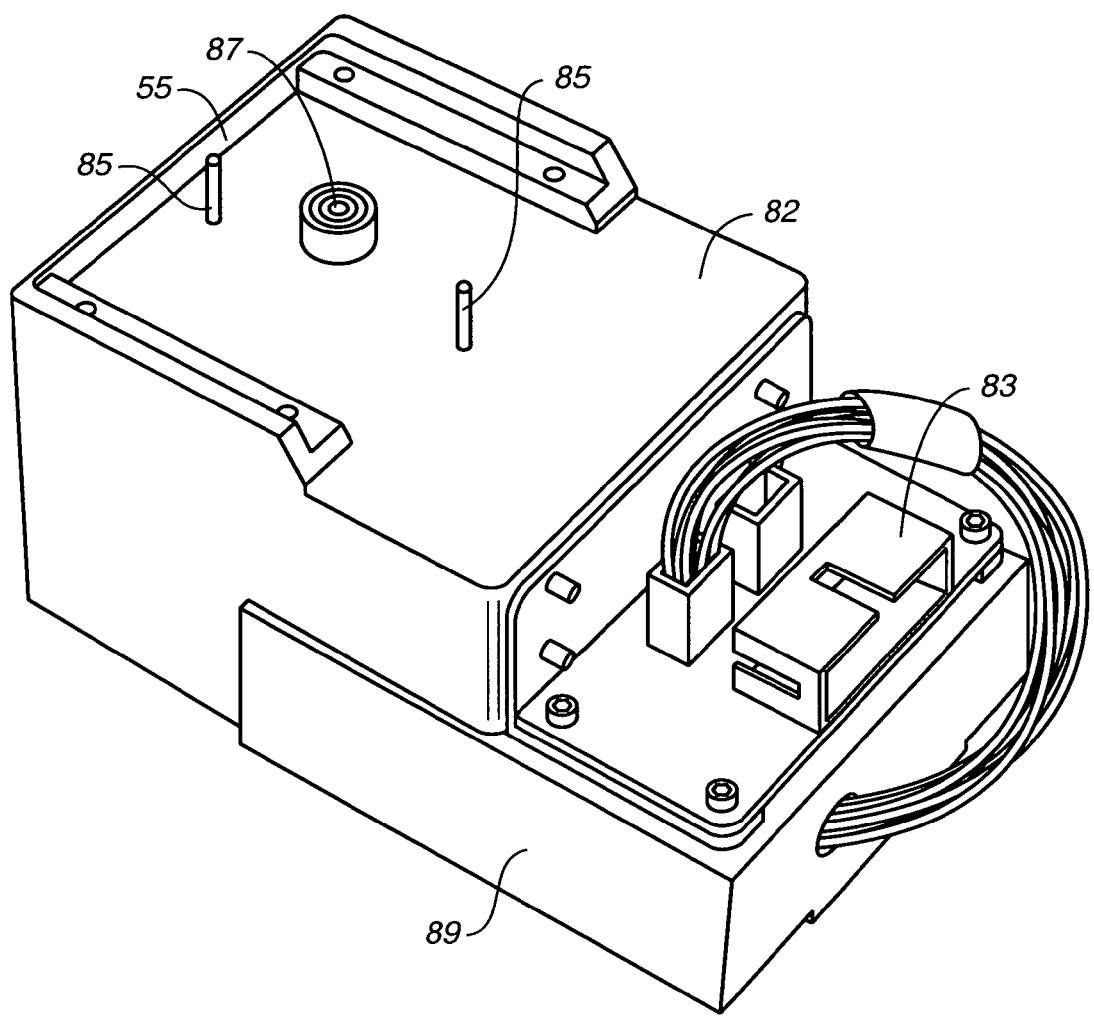
FIG._11A

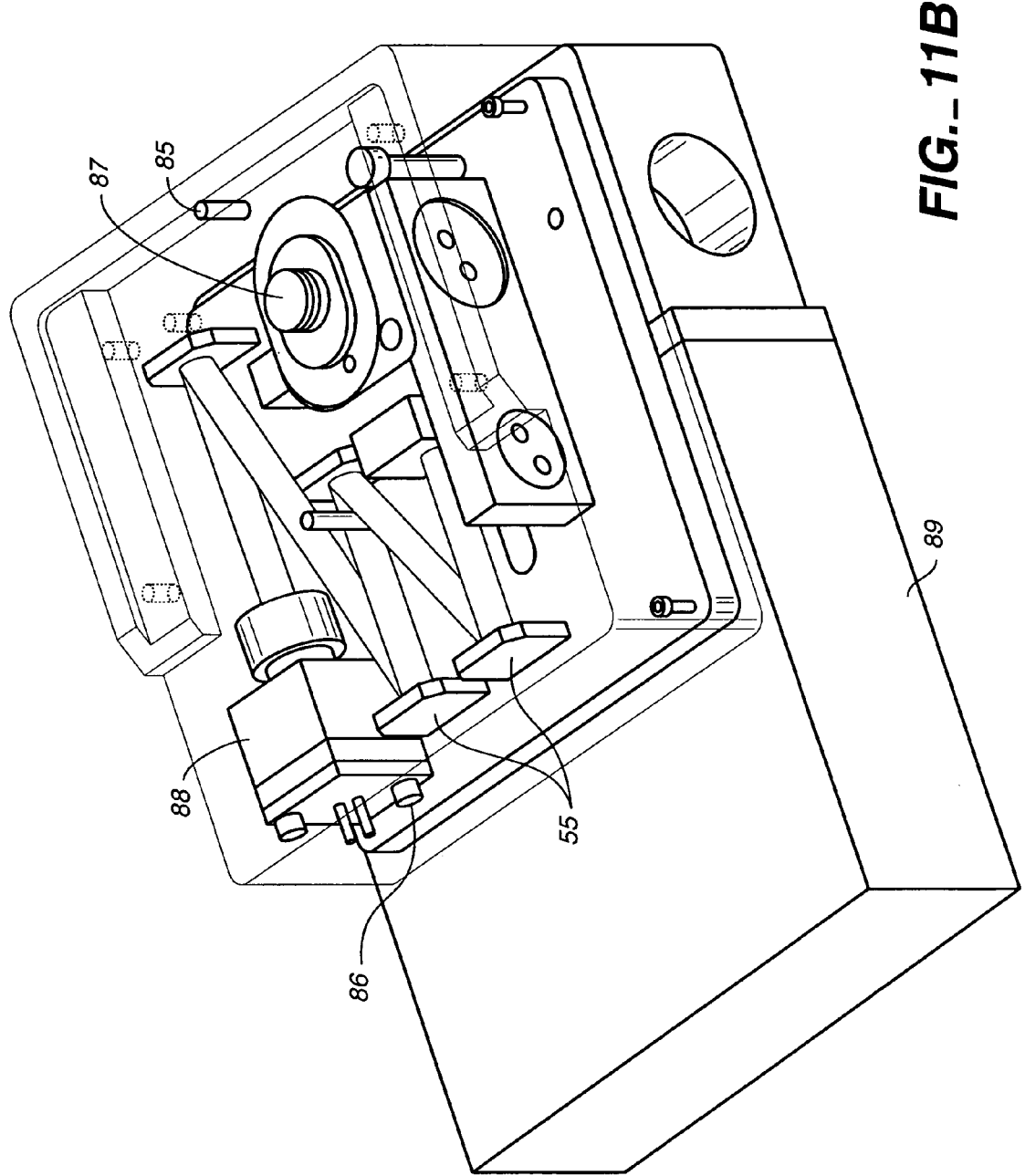
FIG._11B

PORTABLE APPARATUS FOR SEPARATING SAMPLE AND DETECTING TARGET ANALYTES

CROSS-REFERENCE TO RELATED APPLIATIONS

This application claims the benefit of the filing date of U.S. Provisional Application 60/400,884, filed 2 Aug. 2002, entitled "A Modular Device for Microscale Biotoxin Detection", hereby incorporated by reference in its entirety.

STATEMENT REGARDING FEDERALLY-FUNDED RESEARCH

This invention was made with government support under contract No. DE-AC04-94AL85000 awarded by the U.S. Department of Energy to Sandia Corporation.

FIELD OF THE INVENTION

The invention relates to the detection of target analytes in a sample fluid, particularly to a modular device used to detect target analytes in a sample fluid.

BACKGROUND OF THE INVENTION

Devices for manipulating fluids on the microscale have been developed to store, hold, and manipulate small amounts of fluids and have been applied to the detection of analytes in sample fluids. For example, capillary electrophoresis, generally involving the separation of charged species in solution, can be advantageously performed in a microchannel—see for example WO 96/04547, incorporated herein by reference. Electrokinetic and electroosmotic forces have been used to manipulate fluids in microfluidic devices, see WO 96/04547 for example. Manipulating fluids and performing capillary electrophoresis in microfluidic devices promises advantages of small size, high throughput, low sample volumes, and cost.

However, the performance offered by present microfluidic devices is limited by the interfaces between the microfluidic device and the macroscopic world. Connecting detection units including light sources and other detectors, power sources necessary for any actuators or detectors, and macroscopic amounts of reagent fluid and/or sample fluid to present microfluidic devices is cumbersome—often requiring a lengthy process of trial and error or limiting the use of the microfluidic device to one reagent source, or to one detector, or to a single configuration.

Further, although microfluidic devices themselves can have a small form factor, once they are connected to the systems required for their operation—including voltage sources, macroscopic fluid sources, and detectors—the entire system can become too large to be portable.

There is therefore a need for a system that manipulates fluid to detect target analytes on the microscale while providing flexibility to use any of a variety of desired macroscopic parts—including, for example, reagent reservoirs, voltage systems, detectors, and the like. Such a system would desirably be portable.

SUMMARY OF THE INVENTION

According to a first aspect of the present invention, a modular apparatus is provided that includes a reservoir module. The reservoir module includes a fluid manifold base coupled to a plurality of reservoirs. The modular apparatus also includes a microfluidic chip having a plurality of inlets and a separation channel in fluid communication with at least one of the inlets. A seal is positioned between the fluid manifold base and the microfluidic chip to define at least one area of fluidic communication between one of the reservoirs and an inlet. A detection module is positioned within the device to interrogate at least a portion of the separation channel, and an output interface is in communication with the detection module to indicate detection of the target analyte.

According to another aspect of the present invention, a method for resetting a reservoir in a portable device for target analyte detection is provided. A first reservoir is placed in fluid communication with an inlet of a microfluidic chip. The first reservoir is removed from fluid communication with the microfluidic chip. A second reservoir is placed in fluid communication with the inlet of the microfluidic chip. Removing the first reservoir and placing the second reservoir maintains a contiguous fluid stream between an inlet of the microfluidic chip and a separation channel within the chip.

According to another aspect of the present invention, a method for determining the presence of a target analyte in a sample using a portable device comprising a sample introduction port and an output interface is provided. A plurality of reservoirs is coupled to a microfluidic chip within the portable device through a fluid manifold base. The input port is contacted with the sample. A microfluidic separation is performed according to a first separation characteristic within said portable device using at least a portion of said sample. A first separated component of the sample is detected, based on the microfluidic separation. The target analyte is identified, based on the detected component, and detection is indicated on the output interface.

According to another aspect of the present invention, a portable device of analyzing a liquid sample is provided. The device includes a housing including a top plate, a bottom plate, and a back plate. The housing encloses means for receiving the liquid sample and an analysis module including a module for separating the sample into its components, said module in fluid communication with said receiving means and a module for detecting the separated components by producing and acquiring a signal. The housing further encloses means for supplying high voltage to said analysis module, means for converting the signal into an elution spectrum and means for the display of the elution spectrum.

BRIEF DESCRIPTION OF THE DRAWINGS

FIG. 1 depicts a reservoir module, according to an embodiment of the present invention.

FIG. 2 depicts a microfluidic chip, according to an embodiment of the present invention.

FIG. 3 depicts a detection module, according to an embodiment of the present invention.

FIG. 4 depicts an exploded view of a portable device, according to an embodiment of the present invention.

FIG. 5 is a view of the under side of a cover plate showing the arrangement of the main control and high voltage boards, according to an embodiment of the present invention.

FIG. 6 is a view of the back of a device showing a method of pressure injection of a sample, according to an embodiment of the present invention.

FIG. 7 shows a rear view of the device with the back cover removed, according to an embodiment of the present invention.

FIG. 8 shows the components of an analysis module, according to an embodiment of the present invention.

FIG. 9 is an exploded view of a separation module, according to an embodiment of the present invention.

FIG. 10 shows the arrangement of a microfluidic chip, according to an embodiment of the present invention.

FIGS. 11a and 11b are views of the detector module, according to an embodiment of the present invention.

DETAILED DESCRIPTION OF THE INVENTION

Figure 12:
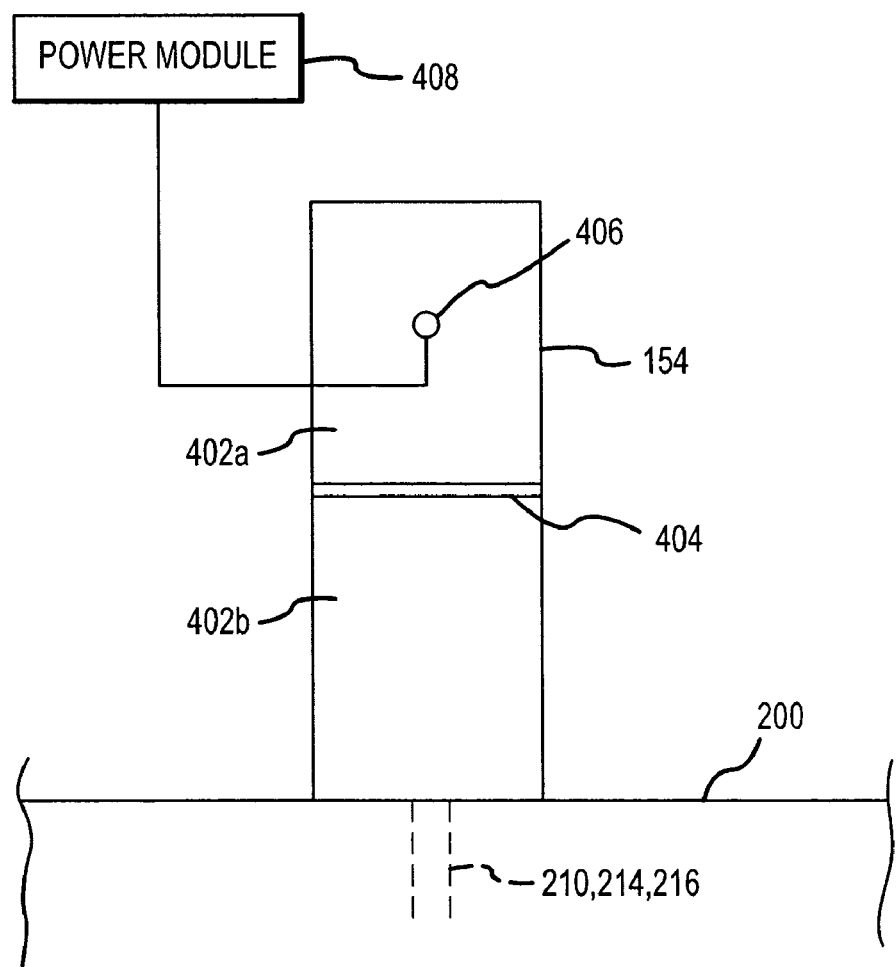
FIG. 12 is a schematic view of a reservoir having multiple chambers, according to an embodiment of the present invention.

Embodiments of the present invention provide portable devices and methods for determining the presence of a target analyte using a portable device. The portable device is preferably hand-held or otherwise able to be transported to a site for sample collection. Such a portable device would be useful, for example, for use by a first-responder such as a fireman, policeman, medical worker, or the like in determining the presence of a biotoxin or other threat. Generally, in embodiments of the invention, a sample is injected to the portable device. A microfluidic separation is performed within the portable device and at least one separated component detected by a detection module within the portable device, in embodiments of the invention. A target analyte is identified, based on the separated component, and the presence of the target analyte is indicated on an output interface of the portable device, in accordance with embodiments of the invention.

In some embodiments, a plurality of separations is performed on the sample to enhance or verify the identification of the target analyte. In some embodiments, the portable device is modular and various components—including, for example, the detection module—can be removed and replaced between separations. Further, in some embodiments a plurality of samples can be analyzed sequentially, and/or simultaneously with the previous samples being stored in a waste reservoir, as is described further below. In some embodiments, the microfluidic separation is performed in a separation channel having a low-dispersion curve. Generally, as described further below, a low-dispersion curve limits the dispersion of a separated component as it traverses the separation channel, thereby enhancing the ability to accurately detect the component. In some embodiments, one or more reservoirs are in fluid communication with a microfluidic chip within the device through a fluid manifold base. This allows one or more reservoirs to be removed and replaced without introducing gas to the microfluidic chip. A general description of a device having subsystems useful with embodiments of the present invention is also found in G. A. Thomas, et. al. "μChemLab™—an integrated microanalytical system for chemical analysis using parallel gas and liquid phase microseparations" Proc. SPIE Vol. 3713, p. 66-76, Unattended Ground Sensor Technologies and Applications, Edward M. Carapezza; David B. Law; K. Terry Stalker; Eds., July 1999, hereby incorporated by reference in its entirety.

Accordingly, the present invention provides methods and devices for determining the presence of a target analyte. By "target analyte" or "analyte" or grammatical equivalents herein is meant any molecule or compound to be detected, defined below. Generally any target analyte that is detectable using the separation methods described further below may be used. Suitable analytes include, but are not limited to, small chemical molecules such as environmental, clinical chemicals, pollutants, toxins (e.g. sarin), and biomolecules, including, but not limited to, pesticides, insecticides, toxins (including biotoxins), therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including procaryotic (such as pathogenic bacteria) and eucaryotic cells, including mammalian tumor cells), viruses, spores, etc.

In preferred embodiments, the target analyte comprises a biotoxin. As will be appreciated by those in the art, there are a large number of possible biotoxins that may be identified using embodiments of the present invention, including, but not limited to, ricin, botulinum toxin, tetanus toxin, cholera toxin, abrin, aflotoxins, and conotoxins.

In preferred embodiments, the target analyte comprises a weapon degradation product. Degradation products that may be identified using embodiments of the present invention include, but are not limited to, alkylphosphonic acids and related monoesters.

In preferred embodiments, the target analyte comprises an explosive. Explosives that may be identified using embodiments of the present invention include, but are not limited to, RDX, HMX, tetryl, trinitrotoluene, other nitrotoluenes and nitroaramines.

In a preferred embodiment, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses or bacteria outlined below.

In a preferred embodiment, the target analytes are nucleic acids, however, in some embodiments, nucleic acids are not preferred target analytes, nor separation components. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids, Koshkin et al., J. Am. Chem. Soc. 120:13252-3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

Suitable target analytes include biomolecules associated with: (1) viruses, including but not limited to, orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like; and (2) bacteria, including but not limited to, a wide variety of pathogenic and non-pathogenic prokaryotes of interest including *Bacillus; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladiu*; and the like.

Other suitable target analytes include, but are not limited to, (1) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (2) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone and testosterone; and (3) other proteins (including α-fetoprotein, carcinoembryonic antigen CEA, cancer markers, etc.).

Suitable target analytes also include carbohydrates and lipids.

Other suitable target analytes include but are not limited to metal ions, metal ion complexes, inorganic ions, inorganic ion complexes, organometallic compounds and inorganic compounds, particularly heavy and/or toxic metals, including but not limited to, aluminum, arsenic, cadmium, chromium, selenium, cobalt, copper, lead, silver, nickel, or mercury.

Embodiments of the present invention determine the presence of a target analyte in a fluid sample. As will be appreciated by those in the art, the sample fluid may comprise any number of things, including, but not limited to, bodily fluids (including, but not limited to, blood, urine, serum, lymph, saliva, anal and vaginal secretions, perspiration and semen; and solid tissues, including liver, spleen, bone marrow, lung, muscle, brain, etc.) of virtually any organism, including mammalian samples; environmental samples (including, but not limited to, air, agricultural, water and soil samples); biological warfare agent samples; research samples (e.g., in the case of nucleic acids, the sample may be the products of an amplification reaction; or in the case of biotoxins, control samples, for instance; purified samples, such as purified genomic DNA, RNA, proteins, etc.; raw samples (bacteria, virus, genomic DNA, etc.). As will be appreciated by those in the art, virtually any experimental manipulation may have been done on the sample prior to its use in embodiments of the present invention. For example, a variety of manipulations may be performed to generate a liquid sample of sufficient quantity from a raw sample. In some embodiments, gas samples and aerosol samples are passed through a collector to generate a liquid sample containing target analytes present in the original sample. In this manner, environmental sampling of gas and/or aerosols may be used. In some embodiments, a liquid may be contacted with a solid sample to disperse the target analyte into the liquid for subsequent analysis.

Embodiments of the invention provide portable devices and methods for detecting a target analyte using a portable device. By 'portable' herein is meant that the device—including a microfluidic chip, detection module, and power supply, as described further below, for performing one or more microfluidic separations—is able to be transported to a site of sample collection. Accordingly, the microfluidic separation is able to be performed at the site of sample collection—a battle field, an accident scene, a doctor's office, an ambulance, or any other location where a sample is collected. In some embodiments, however, the device is portable, but remains located in a central location and samples are brought to the device. In some embodiments, the device is temporarily or permanently affixed to a non-portable structure, such as a wall, pipe, tank, building, office, factory, stadium or other structure, etc. and samples are brought to or taken by the device. For example, the device may be used as a detector in communication with a sensing module, as is described in U.S. patent application Ser. No. 10/402,383, filed 28 Mar. 2003 entitled "Systems and Methods for Detecting and Processing", hereby incorporated by reference in its entirety. The output interface of the device may be coupled to the sensing module, in one embodiment. Briefly, the sensing module includes a processor and wireless modem. The sensing unit may be in communication with one or more other sensing units for communicating data collected by one or more embodiments of portable devices according to the present invention. In some embodiments, the sensing module is configured to model data to be generated by an embodiment of the portable device according to the present invention.

In preferred embodiments, the device is hand-held, that is able to be carried by a single individual, preferably by hand, to a location. Accordingly, in preferred embodiments, the portable device weighs between 1 to 10 pounds, more preferably between 3 and 4 pounds. In preferred embodiments, the portable device is between 500 and 3,000 cubic centimeters in volume, more preferably between 500 and 1,500 cubic centimeters, and most preferably about 1 liter in volume. This facilitates use, for example, by first-responders such as firemen, policemen, and medical workers. In other embodiments, the device is carried in a backpack, belt strap, suitcase or other personal carrying device. In other embodiments, the portable device is transported by a vehicle. The portable device has an input port and an output interface. In some embodiments the input port and output interface are not contained within the same housing. For example, in some embodiments the modules needed to perform a microfluidic separation—including an inlet, microfluidic chip, detector module, power module, and reservoir module, as described further below—are positioned in a sample collection location, and may be mobile (for example, by autonomous or remote control)—for example, taking a sample in an location inaccessible or dangerous for a person or other reader of the output interface, and sending data relating to the microfluidic separation to an output interface in a different location. The output interface and modules needed to perform microfluidic separation, in such embodiments, are in communication via electronic, optical, or wireless means, as known in the art. In preferred embodiments, the device is self-powered, for example, by batteries, as known in the art.

Embodiments of portable devices according to the present invention accordingly include a plurality of modules. By 'module' herein is meant one or a collection of components configured to perform a function that is preferably interchangeable within the device. In some embodiments, one or more of the modules are modular, meaning the module can physically be removed from the device and a different or replacement module positioned in its place. However, in some embodiments two or more modules are integrated together in such a way that they are not removable from the device. In this embodiment, it is preferred that the device have at least one interchangeable module, although this may not be necessary in some instances, e.g. for dedicated uses.

Briefly, embodiments of a portable device according to the present invention comprise a sample introduction port, a reservoir module, a microfluidic chip, a power module, a detection module, CPU controller or other processor and or/control software, and an output interface. In some embodiments, one or more of those modules are not present. In accordance with some embodiments, the interfaces between modules are standardized, such that individual modules can be disconnected, or removed from their position and replaced.

For example, as described further below, in some embodiments, the microfluidic chip includes a plurality of inlets, as described further below, for fluid communication with one or more reservoirs and/or sample introduction ports. The reservoir module, as described further below, comprises a plurality of reservoirs. The reservoir module, as described further below, includes a plurality of reservoirs coupled to a fluid manifold base, which in turn is coupled to a microfluidic chip. The reservoirs are coupled to the fluid manifold base in such a way that one or more reservoirs may be removed and replaced (with the same or a different reservoir) without introducing gas, e.g. a bubble, into the microfluidic chip. In some embodiments, each reservoir comprises a seal and the reservoir module comprises one or a plurality of needles, each piercing the seal of a reservoir to facilitate fluidic communication with inlets on the microfluidic chip, in accordance with embodiments of the present invention. In some embodiments, one or more of the reservoirs are provided with an electrode for electrical communication between the power module and the contents of the reservoir. The detection module is positioned and configured to detect one or more target analytes on or in the microfluidic chip, as described further below. The power module is in electronic communication with the reservoir module, microfluidic chip, and/or detection module, as needed, in embodiments of the invention. The detection module is positioned to detect target analytes in or on the microfluidic chip. For example, in one embodiment the detection module includes an optical source and is positioned such that the light source illuminates a detection area on the microfluidic chip and illumination from the microfluidic chip is received by the detection module. The detection module may be in further communication with the power module, as needed. Some embodiments of the invention include a processor and user interface, as described further below. The processor is in communication with the power module, detection module, and/or output interface as needed in embodiments of the invention.

The interconnected modules are, in some embodiments, preferably placed into a single housing, as described further below. The modules are preferably positioned in the housing such that they are removable. For example, in some embodiments the power module is affixed to a processor board, and installed into the housing. In one embodiment, the detection module is affixed to the housing through a dove-tail rail, or other removable mechanism, as known in the art. The reservoir module is mounted above the detection module, in one embodiment. As described further below, it is to be understood that any number of physical methods of integration of the modules may be used—mechanical screws, flanges, rails, slots, connectors, and the like—while maintaining features of one or more of the modules that allow the integration.

In embodiments of the present invention, the reservoir module comprises a plurality of reservoirs. Any number of reservoirs may generally be provided, and the number will vary based on the application, the size of the reservoirs, the desired size of the resultant device, the chip being used, and the like. In one embodiment, between 1 and 10 reservoirs are provided, although a fewer or greater number of reservoirs may also be used. The reservoirs each contain a fluid and a seal. In a preferred embodiment, the reservoir contains a macroscopic amount of fluid—that is, greater than 20 µL of fluid. In some embodiments, each reservoir is configured to contain between 20-5000 µL of fluid, more preferably between 100 and 1,000 µL, more preferably between 200-500 µL. Of course, in some embodiments a reservoir configured to contain a greater or smaller amount of fluid may be provided. In some embodiments, the reservoir module includes one or more reservoirs configured to contain a microscopic amount of fluid—such as an amount of fluid less than 20 µL. However, it is desirable that the reservoir module itself be macroscopic such that a user could manipulate, remove, and/or replace the reservoir module by hand, or by a robotic system.

In some embodiments, a reservoir comprises one or more chambers. In some embodiments, the chambers are in fluidic communication, however, in some embodiments fluids are confined to the individual chambers. In some embodiments, the chambers are in electronic communication; however, in some embodiments the individual chambers are electronically isolated. In a preferred embodiment, a reservoir comprises two chambers separated by a barrier, such as, for example, an ion permeable membrane, salt bridge, dialysis membrane, polymer film, diffusion membrane, ionomer, e.g. NAFION® from Dupont, nanoporous glass, e.g. VYCOR® from Corning, and/or the like. In some embodiments, one chamber contains a fluid to be contacted with the microfluidic chip. A second chamber contains a fluid in contact with an electrode and is not in fluid communication with the microfluidic chip. The barrier permits electrical communication between the two chambers, in this embodiment, and prevents fluidic communication between the chambers. In this manner, fluid entering the microfluidic chip is not altered by any effects of applying a voltage across the fluid, such as pH change.

The particular fluid contained by a reservoir varies according to the application contemplated. Reservoirs generally contain reagents desired for use on a microfluidic chip, including but not limited to salts, buffers, neutral proteins (e.g. albumin), detergents, water, organic liquids with one or more components, polymers, surfactants, etc. which may be used to facilitate optimal reaction conditions and/or detection conditions, as well as optionally reduce non-specific or background interactions. Also reagents that otherwise improve the efficiency of the assay, such as protease inhibitors, nuclease inhibitors, anti-microbial agents, etc., may be used, depending on the sample preparation methods and purity of the target. Reservoirs may also contain separation media, as described further below. Preferred reagents for positioning in the reservoirs include, but are not limited to borate buffer, carbonate buffer, phosphate buffer, Tris buffer, phytic acid buffer, protein or DNA sieving gels, additives such as SDS, and other surfactants.

Generally, one or more reservoirs are coupled to the microfluidic chip by the fluid manifold base, described above. In some embodiments, a reservoir comprises a connector such as a hollow threaded connector, a tube with a gasket or o-ring, and the like. The fluid manifold base comprises a complimentary structure for the structure on the exterior of the reservoir. The fluid manifold base transports fluid from the reservoir through the structure to the microfluidic chip. The connector on the reservoir may or may not freely evolve fluid when not connected to the fluid manifold base. The connector on the reservoir or the complimentary structure on the fluid manifold base can comprise a valve and/or a seal, in some embodiments. The connector and/or complimentary structure may comprise one or more individual components comprised of the same or different materials. When a reservoir and the fluid manifold base are mated the connection provides a leak-free, contiguous fluid communication between the reservoir and the microfluidic chip. For example, in some embodiments, the structure on the bottom surface of the reservoir comprises a needle as described above. The complimentary structure attached to the microfluidic chip comprises an interface that is comprised of a seal in similitude to the seal for the bottom of the reservoir, described below. A leak resistant, contiguous fluid communication between the reservoir and the fluidic chip is formed by piercing the seal of the microfluidic chip with the needle connection of the reservoir. For example, in some embodiments, the structure on the bottom surface of the reservoir is a hollow, threaded mechanical fitting. The complimentary structure attached to the microfluidic is a hollow connector for mating to the threaded fitting on the reservoir. A leak resistant, contiguous fluid communication is formed by screwing the reservoir into the microfluidic chip.

In some embodiments, each reservoir within the reservoir module contains a seal for interface with the microfluidic chip, described below. The seal prevents or minimizes evaporation of the fluid in the reservoir and prevents leakage or spillage of fluid from the reservoir during operation and/or during removal of the reservoir or of the reservoir module from the apparatus, or during the assay. However, in most embodiments, the seal must also allow penetration of a needle into the individual reservoir. Accordingly, the seal can be a cap, lid, polymer, membrane, bipolymer membrane, septum, thin film polymer, etc. Alternatively, the seal may comprise multiple components, for example a flexible polymer through which a needle will go, attached to the reservoir vial with an adhesive. In some embodiments, the seal comprises a valve, as described further below.

Reservoirs may be made from any of a number of materials, including, but not limited to, Teflon, polyetheretherketone, polyfluoroethylene, polyoxymethylene, polyimide, polyetherimide, other polymer materials, glass, fused silica and/or ceramic. Preferred materials for reservoir construction are transparent or semitransparent, in order to be able to view the fluid levels in the reservoirs. Preferred materials further have low conductivity and high chemical resistance to buffer solutions and/or mild organics used for separation media.

In some embodiments, the reservoir module includes a reservoir base which defines at least one depression or hole defining a reservoir, or into which a reservoir may be placed. For example, the reservoir base may be configured to receive a plurality of different reservoirs, such as vials, comprising reagents and/or sample or other fluid. In embodiments of the invention, the holder and the vials may be made of the same or different materials. Reservoir base materials may include, but are not limited to, the same materials used for reservoirs, described above, other machinable or moldable polymeric materials, insulators, ceramics, metals or insulator-coated metals. In a preferred embodiments, the reservoir and reservoir base materials are constructed from a polymer material that is resistant to alkaline aqueous solutions and mild organics.

In some embodiments, the reservoir base of the reservoir module defines at least one reservoir, that is, the reservoir and reservoir base are one contiguous piece. Accordingly, in some embodiments the fluid in the reservoirs is in direct contact with the reservoir base, and in other embodiments the fluid is contained in another reservoir that is placed into the reservoir base. Generally, any material suitably mechanically stable for defining at least one reservoir or depression and holding the reservoirs such that the needles in the fluid manifold base and/or on the microfluidic chip may be inserted into the reservoirs, may be used.

Embodiments of the reservoir module further include a fluid manifold, comprising a fluid manifold base and a compression plate, in embodiments of the invention. In some embodiments, the fluid manifold is continuous with the reservoir base, and in other embodiments, the fluid manifold is a separate component, formed from a same or different material as the reservoir base, and affixed to the reservoir base with adhesives and/or mechanical means, for example screws or magnets. The fluid manifold, in some embodiments, comprises a fluid manifold base defining a plurality of depressions with which the reservoirs, as defined by the reservoir base, are in fluid communication. In some embodiments, the reservoirs are inserted into the reservoir base, and further protrude into the fluid manifold. In other embodiments, the depressions defined by the reservoir base are contiguous with depressions defined by the fluid manifold base. The depressions in the fluid manifold base may be smaller, larger, or the same size as depressions defined by the reservoir base. The fluid manifold base generally serves to provide a leak-free (or low-leakage), electrically resistive, confinement pathway for liquid to traverse from one or more reservoirs to the microfluidic chip.

As described above, in some embodiments the fluid manifold base includes complementary structures to those found on one or more reservoirs, to facilitate mating the reservoirs to the fluid manifold base. In some embodiments, the fluid manifold base contains a needle that penetrates a seal of a reservoir placed in the fluid manifold base. The needle can generally be any sturdy tube, or other hollow cross-section, that can pass fluid from the reservoir to the microfluidic chip. It can be blunt, rounded, or sharp tipped. The tip may have a convex or concave shape, in accordance with embodiments of the present invention. The mechanical properties of the exposed tip of the needle have sufficient hardness and sharpness to penetrate the seal on the reservoir (or enter a pierced hole on the reservoir seal) without breaking. The needle allows a contiguous fluid stream to pass from the reservoir to the microfluidic chip, in some embodiments. Accordingly, the particular diameter of the needle may vary according to the particular fluid and application contemplated. The needle may be made of metals, polymers, glass, ceramics, semiconductors, or the like, as known in the art. The needle material may be modified from the original material to provide a more reliable connection through the reservoir seal. For example, the outside surface of a capillary may be chemically modified to increase the surface tension of the capillary/reservoir seal interface to reduce the rate of leakage, in some embodiments. The material and dimensions of the needle are chosen so that the needle maintains a contiguous fluid stream after the reservoir is reset (or removed). That is, the needle prevents air incursion, such as a bubble, into the microfluidic chip when removing and/or replacing a reservoir or the entire reservoir base. In a preferred embodiment, one or more needles are made of fused silica coated with polyimide. The needle is positioned such that it is in fluidic communication with one or more inlets of the microfluidic chip, as described further below. Further, the presence of the needle allows for a reservoir to be removed and replaced without the introduction of a bubble into the fluid stream.

Needles may include one or more components, in accordance with embodiments of the invention. The individual components are made from the same or different materials. One or more of the individual components pierces the seal of the reservoir. One or more of the components is involved with creating a leak resistant interface between the needle and the seal of the reservoir. The individual components of the needle are connected by mechanical, physical and/or chemical means including, but not limited to, adhesives such as epoxies or glues, melting, welding, soldering, clamping, compressing or fusing. The individual components of the needle are connected to one or more of the individual components of the needle.

In preferred embodiments, polymer fitting are used to attach the needle to the chip and/or the fluid manifold base. Fitting suitable for use with the present invention are described further, for example in U.S. application Ser. No. 10/405,842, filed 2 Apr. 2003, entitled "Micromanifold Assembly", U.S. patent application Ser. No. 10/405,204, filed 2 Apr. 2003 entitled "High Pressure Capillary Connector," U.S. patent application Ser. No. 10/350,626 entitled "Fluid Injection Microvalve," filed 24 Jan. 2003, U.S. patent application Ser. No. 10/351,714, filed 27 Jan. 2003 entitled "Microvalve," U.S. patent application Ser. No. 10/350,541, filed 24 Jan. 2003 entitled "Capillary Interconnect Device," and U.S. patent application Ser. No. 10/350,628, filed 24 Jan. 2003, all of which are hereby incorporated by reference in their entirety. In one embodiment, however, the needle is attached directly to an inlet of the microfluidic chip with an adhesive, for example.

Needles can be attached to the microfluidic chip directly or indirectly. In some embodiments, the needle is attached directly to the inlet of a microfluidic chip by forming a leak resistant seal between the needle and an inlet of the microfluidic chip such that the needle can transport fluid into the microfluidic chip. Methods for attaching the needle to the microfluidic chip include, but are not limited to, adhesives such as epoxies and glues, melting, welding, soldering or fusing. In some embodiments, the needle and inlet of the microfluidic chip are mated via a separate connection. For example, in one embodiment, the connector on the needle can be separate from or contiguous to or attached to the material comprising the needle. A connector complimentary to the needle connector is found attached to the microfluidic chip. The connector and the complimentary connector are comprised of one or more individual components and are comprised from the same or different materials. The complimentary connector to the fitting attached to the needle is machined into the fluidic manifold base, in some embodiments. For example, the needle may be in a fitting that is screwed into the fluid manifold base. The needle and needle connection screw into the complimentary connection in the fluid manifold base and the needle fitting compresses against the needle forming the leak resistant seal.

The fluid manifold base is coupled to a microfluidic chip, as described further below, using a compression plate. The compression plate is configured to support the microfluidic chip and compress it against the fluid manifold base, using structures known in the art, such as screws, clamps, clips, vises, magnets, solenoids, etc. Seals such as o-rings or gaskets are placed between the microfluidic chip and the fluid manifold base such that the microfluidic chip is in fluid communication with one or more needles via one or more input ports on the microfluidic chip, as described further below. The o-rings or gaskets may be formed from any number of materials, including, but not limited to, rubber, silicone, Viton, Buna-N, Teflon, nitrile, neoprene, polyurethane, EPDM, perfluoroelastomer, fluorosilicone, etc. The particular o-ring material chosen is dependent on the chemical resistance of the material to the liquid media used, in some embodiments. In embodiments using o-rings, the o-rings are positioned around one or more input ports of the microfluidic device such that fluidic communication is established between the microfluidic device and a reservoir. The compression plate generally provides a surface for an evenly distributed compression force to be applied to the microfluidic chip for sealing against the o-rings or gaskets. The compression plate can be made form any material with sufficient toughness to withstand the compression forces required to hold the chip against the o-rings—including, for example, glass, polymer, metal, semiconductor, insulator, ceramic, and the like.

In some embodiments, the compression plate comprises one or more separate parts used to compress the microfluidic chip against the fluid manifold base. In embodiments where the compression plate comprises more than one separate part, the individual parts can be made from the same or different materials. The compression plate can be opaque, semitransparent or transparent. In preferred embodiments, one part of the compression plate is transparent, such as glass. For example, the compression plate can be made from two parts—a metal frame and a glass plate, in some embodiments. In some embodiments, the compression plate contains mechanical features, such as depressions, tabs, or holes to accommodate the modular nature of the device. In a preferred embodiment, the compression plate contains a hole that allows access to the separation channel of the microfluidic chip by the detection module. In a preferred embodiment, the compression plate includes depressions for metal pins used for alignment of the reservoir module to the detection module.

In some embodiments, as described further below, the reservoir module further comprises an introduction port. In some embodiments, the introduction port is the sample introduction port for the portable device. In other embodiments, the fluid manifold introduction port is in fluid communication with a sample introduction port in an external housing, through tubing, channels, or other means known in the art, for example when a gaseous or aerosol sample is being collected. In some embodiments, a plurality of introduction ports is provided. The introduction port, in some embodiments, is placed on one side of the fluid manifold base. One or more channels are provided in the fluid manifold base coupling the introduction port to one or more input ports on the microfluidic device. In preferred embodiments, the channel is as short as can be formed in the fluid manifold base to minimize the amount of fluid necessary to fill the channel. In a preferred embodiment, an injector port has a sample injector volume between the port and the microfluidic chip of less than 1500 nanoliters, more preferably less than 1000 nanoliters, still more preferably less than 500 nanoliters, and most preferably about 50-100 nanoliters. In a preferred embodiment, for example, the sample fluid containing a target analyte of interest is injected into the microfluidic device through the introduction port in the fluid manifold base. Embodiments of the introduction port can accommodate, for example, a standard syringe, tubing, pumps such as electrokinetic pumps, peristaltic pumps, hydrostatic pumps, displacement pumps, balloon, bladder, or any other injection mechanism as known in the art—including simply contacting the introduction port with a sample, such as by spitting. In some embodiments, an introduction port is provided in fluidic communication with a channel in the fluid manifold base that connects to one or more reservoirs in the reservoir module. Accordingly, in preferred embodiments, one or more reservoirs may be filled, refilled, or added to by injecting fluid into an introduction port.

Further, in preferred embodiments, one or more reservoirs in the reservoir module contain an electrode 406 (see FIG. 12) for interconnection to the power module 408, described further below. The electrode is positioned to be in contact with the fluid contents of one or more reservoirs. In this manner, fluid may be transported within the microfluidic chip by the application of voltages to one or more electrodes in reservoirs, in accordance with embodiments of the invention. For example, in some embodiments, a contiguous fluid stream exists between two reservoirs through one or more channels in the microfluidic device. By applying a voltage or current between the two reservoirs, fluid is transported toward one of the reservoirs, determined by the polarity of the voltage or current application and the fluid used.

Accordingly, an electrode may be positioned in or on a reservoir in generally any way allowing electrical contact with the fluid contents and the power module. In some embodiments, the electrode is affixed to the reservoir base, and extends into the reservoir. In some embodiments, the electrode is affixed to the fluid manifold base, and extends into the reservoir. In some embodiments one or more needles, as described above, serve as an electrode in contact with the reservoir fluid. In one embodiment, where a reservoir is provided that is placed into the reservoir base, the electrode is provided on a reservoir cap that is mechanically coupled to the reservoir. For example, a reservoir cap may screw onto, or fit over the top of a reservoir that is placed into the reservoir base. The reservoir cap comprises an electrode extending into the reservoir and an interconnect accessible from the outside of the cap. The cap may be formed from a variety of materials, preferably insulating materials. However, in some embodiments the cap is a conductive material and the entire cap forms an electrode, with a portion extending into the reservoir. The electrode may be formed from any of a variety of conductive materials including metals such as gold, tungsten, aluminum, platinum, porous carbon, and the like. In preferred embodiments, the electrode material is chosen such that any reaction between the electrode and the fluid in the reservoir is minimized.

The composition of the reservoir module (either the whole block or the base and the vials), can be made of a wide variety of materials, generally the same materials that comprise the chip, described below. In general, any material can be used, with materials that are in direct contact with the fluids in the reservoirs being preferably chemically inert. Suitable materials include glass and modified or functionalized glass, fiberglass, teflon, ceramics, mica, plastic (including acrylics, polystyrene and copolymers of styrene and other materials, polypropylene, polyethylene, polybutylene, polyimide, polycarbonate, polyurethanes, Teflon(tm), and derivatives thereof, etc.), GETEK (a blend of polypropylene oxide and fiberglass), etc., polysaccharides, nylon or nitrocellulose, resins, silica or silica-based materials including silicon and modified silicon, carbon, inorganic glasses and a variety of other polymers, as also described above. The use of conductive materials has limited application, in some embodiments.

One embodiment of a reservoir module according to the present invention is shown in FIG. 1. Reservoir module 150 includes reservoir base 152 configured to accommodate a plurality of reservoirs in depressions 153. Although shown as cylindrical, the reservoirs may take generally any shape—including square, rectangular, and the like. The fluid may be in direct contact with reservoir base 152, for example, contained in depressions or holes in base 152, or may be provided as separate reservoirs, such as a reservoir 154, and placed in the reservoir base 152. A fluid manifold base 155 is provided, as described above to facilitate a fluid path between reservoirs and a microfluidic chip 160. The fluid manifold base 155, in one embodiment, further supports one or more needles 159, where each needle penetrates a seal 161 of a reservoir 154. In some embodiments, as described above, the needle 159 is secured in the fluid manifold base 155 using a polymer fitting that, for example, screws into the fluid manifold base 155. An introduction port 156 is preferably provided for sample injection or coupling to an external reservoir. In a preferred embodiment, the introduction port 156 is formed in one side of the fluid manifold base 155, and a channel is formed in the fluid manifold base 155 leading from the introduction port 156 to the microfluidic chip 160. In a preferred embodiment, one or more of the reservoirs contains an electrode, such as electrode 157, and the electrodes are coupled to the power module through electrode plate 158, described further below. The reservoir module 150 is coupled to a microfluidic chip 160, as described further below. As will be described further below, the microfluidic chip 160 comprises at least one inlet (or outlet) 161. The reservoir module 150 is coupled to the microfluidic chip 160 such that fluidic communication is established between reservoir module 150 and the microfluidic chip 160 via an inlet (or outlet) 161.

In a preferred embodiment, and in accordance with microfluidic separation techniques, the reservoir module 150 comprises a channel flush port, sample reservoir, a sample waste reservoir, a buffer reservoir, and a buffer waste reservoir. The sample reservoir contains a sample electrode, the sample waste reservoir contains a sample waste electrode, the buffer reservoir contains a buffer electrode, and the buffer waste reservoir contains a buffer waste electrode. Each reservoir, in embodiments of the invention, is in fluid communication with an inlet or outlet port on the microfluidic chip, described further below.

In one embodiment, the channel flush port is connected to a syringe and is in fluidic communication with a channel flush inlet and flush channel of the microfluidic chip. The channel flush port serves as an access point for introducing the separation medium onto the microfluidic chip for the purpose of filling or exchanging the separation medium. In another embodiment, the channel flush port can serve as an access point for evacuating the separation medium from the microfluidic chip.

Embodiments of reservoir modules and injectors useful in the present invention and/or useful in coupling a reservoir module to a microfluidic chip, are further described in, for example, U.S. patent application Ser. No. 10/405,842, filed 2 Apr. 2003, entitled "Micromanifold Assembly", U.S. patent application Ser. No. 10/405,204, filed 2 Apr. 2003 entitled "High Pressure Capillary Connector," U.S. patent application Ser. No. 10/350,626 entitled "Fluid Injection Microvalve," filed 24 Jan. 2003, U.S. patent application Ser. No. 10/351,714, filed 27 Jan. 2003 entitled "Microvalve," U.S. patent application Ser. No. 10/350,541, filed 24 Jan. 2003 entitled "Capillary Interconnect Device," U.S. patent application Ser. No. 10/350,628, entitled "Edge Compression Manifold Apparatus," filed 24 Jan. 2003, and U.S. Pat. No. 6,290,909, entitled "Sample Injector for High Pressure Liquid Chromatography", all of which are hereby incorporated by reference in their entirety.

Embodiments of the present invention include a microfluidic chip, such as the microfluidic chip 160 shown in FIG. 1, configured to be coupled to the reservoir module. By 'microfluidic chip' herein is generally meant a substrate configured for handling small amounts of fluid, generally nanoliters, although in some applications a larger or smaller fluid volume will be necessary. As is known in the art, microfluidic chips are generally constructed substantially of a substrate. The substrate can be made of a wide variety of materials and can be configured in a large number of ways, as is discussed herein and will be apparent to one of skill in the art. The composition of the substrate will depend on a variety of factors, including the techniques used to create the device, the use of the device, the composition of the sample, the analyte to be detected, the size of internal structures, the presence or absence of electronic components, and the technique used to move fluid, etc. Generally, the devices of the invention should be easily sterilizable as well, although in some applications this is not required. The devices could be disposable or reusable.

In a preferred embodiment, the substrate can be made from a wide variety of materials including, but not limited to, silicon, silicon dioxide, silicon nitride, glass and fused silica, gallium arsenide, indium phosphide, III-V materials, PDMS, silicone rubber, aluminum, ceramics, polyimide, quartz, plastics, resins and polymers including polymethylmethacrylate, acrylics, polyethylene, polyethylene terepthalate, polycarbonate, polystyrene and other styrene copolymers, polypropylene, polytetrafluoroethylene, superalloys, zircaloy, steel, gold, silver, copper, tungsten, molybdeumn, tantalum, KOVAR, KEVLAR, KAPTON, MYLAR, teflon, brass, sapphire, etc. High quality glasses such as high melting borosilicate or fused silicas may be preferred for their UV transmission properties when any of the sample manipulation and/or detection steps require light based technologies. In addition, as outlined herein, portions of the internal and/or external surfaces of the device may be coated with a variety of coatings as needed, to facilitate the manipulation or detection technique performed.

Structures within such microfluidic chips—including for example, channels, chambers, and/or wells—generally have dimensions on the order of microns, although in many cases larger dimensions on the order of millimeters, or smaller dimensions on the order of nanometers, are advantageous.

In preferred embodiments of the present invention, microfluidic chips are provided including at least one separation channel. The separation channel is configured to facilitate the chemical or physical separation of species in the channel. Separations of interest include, but are not limited to capillary zone electrophoresis, liquid chromatography, affinity chromatography, capillary gel electrophoresis, isotachophoresis, capillary electrochromatography, micellar electrokinetic chromatography, and isoelectric focusing, as known in the art. Accordingly, in some embodiments, it is desirable to have as long of a channel as feasible given the desired size of the microfluidic chip and resultant device. Accordingly, in one embodiment, a spiral channel is provided having a plurality of concentric loops to increase the length of channel per area of the microfluidic chip. Other configurations include curves, arcs, serpentine configurations, and the like.

Similarly, it is desirable for 'plugs' or 'zones' of, such as a separated component of the sample, to remain distinct as they traverse the separation channel. Accordingly, in some embodiments one or more curves in the separation channel are implemented as low-dispersion curves, described for example in U.S. Pat. No. 6,270,641, PCT Application Number 00/09722, and U.S. patent application Ser. No. 09/707,337, filed 6 Nov. 2000, all of which are hereby incorporated by reference. Briefly, turns, tees and other junctions are provided that produce little dispersion of a sample as it traverses the turn or junction. The reduced dispersion results from contraction and expansion regions that reduce the cross-sectional area over some portion of the turn or junction. Sample dispersion in turns and junctions in then reduced to levels comparable to the effects of diffusion.

In embodiments of the present invention, separation channels are provided being long enough to facilitate the separation of analytes in a fluid. In a preferred embodiment, a 10-cm long separation channel is provided. In other embodiments, the separation channel is between 10 and 30 cm in length, in other embodiments, the separation channel is between 15 and 25 cm in length, and in a preferred embodiment the separation channel is 20 cm in length. Shorter or longer lengths may also be used. The length chosen will vary according to the form factor of the microfluidic chip, sample fluid, electrophoretic media, time desired for separation, and desired resolution of the separation, as known in the art.

Other advantageous channel arrangements and microfluidic chips that may be used with the present invention are described in U.S. Application Publication Number 2003/0075491 entitled "Compact Microchannel System", published 24 Apr. 2003, hereby incorporated by reference, and U.S. patent application Ser. No. 09/669,862 entitled "Method and Apparatus for Controlling Cross-Contamination of Microfluidic Channels", hereby incorporated by reference.

In addition to the separation techniques described above, the microfluidic chip and/or separation channel could be used to perform solid phase extraction, dialysis, sample filtration, analyte labeling, mixing, analyte preconcentration methods, or other sample preparation techniques or other physical or chemical separation techniques, as known in the art. The inlet and outlet ports of the microfluidic device will be placed as needed to perform the desired operation. The separation channel generally serves to separate sample components by the application of an electric field, with the movement of the sample components being due either to their charge or, depending on the surface chemistry of the microchannel, bulk fluid flow as a result of electroosmotic flow (EOF).

As will be appreciated by those in the art, the separation channel generally has associated electrodes to apply an electric field to the channel. Waste fluid outlets and fluid reservoirs are present as required. In some embodiments, electrodes are formed on the chip and are connected to the power module. In some embodiments, no electrodes are placed on the chip, and the electric field is generated across the channel using electrodes in contact with one or more reservoirs, as described above.

In a preferred embodiment, electrophoretic media is placed in the separation channel. By varying the pore size of the media, employing two or more gel media of different porosity, and/or providing a pore size gradient, separation of sample components can be maximized. Gel media for separation based on size are known, and include, but are not limited to, polyacrylamide and agarose. One preferred electrophoretic separation matrix is described in U.S. Pat. No. 5,135,627, hereby incorporated by reference, that describes the use of "mosaic matrix", formed by polymerizing a dispersion of microdomains ("dispersoids") and a polymeric matrix. This allows enhanced separation of target analytes, particularly nucleic acids. Similarly, U.S. Pat. No. 5,569,364, hereby incorporated by reference, describes separation media for electrophoresis comprising submicron to above-micron sized cross-linked gel particles that find use in microfluidic systems. U.S. Pat. No. 5,631,337, hereby incorporated by reference, describes the use of thermoreversible hydrogels comprising polyacrylamide backbones with N-substituents that serve to provide hydrogen bonding groups for improved electrophoretic separation. See also U.S. Pat. Nos. 5,061,336 and 5,071,531, directed to methods of casting gels in capillary tubes.

Further electrophoretic media that may be used in conjunction with embodiments of the present invention may be found in U.S. application Ser. No. 09/310,465, filed 12 May 1999 entitled "Castable 3-dimensional Stationary phase for chromatography" and U.S. Application Publication Number 2001/0008212 entitled "Castable Three-dimensional Stationary Phase for Electric Field-Driven Applications", filed Feb. 28, 2001, both of which are hereby incorporated by reference.

One or more microfluidic chips are coupled to a reservoir module, as described above, according to embodiments of the present invention. Accordingly, the microfluidic chip comprises one or more inlets or outlets to allow fluidic communication with one or more reservoirs, and/or one or more ports, as described above. Inlets and outlets are generally structurally similar, and the terms are used interchangeably herein. Each inlet comprises an area of the microfluidic chip in fluidic communication with one or more channels or chambers. Inlets and outlets may be fabricated in a wide variety of ways, depending on the substrate material of the microfluidic chip and the dimensions used. For example, in one embodiment inlets and/or outlets are formed by removing portions of a sealing layer and affixing the sealing layer to a substrate containing chambers and/or channels such that the removed portions of the sealing layer allow fluidic access to one or more channels or chambers.

One embodiment of a microfluidic chip according to the present invention is shown in FIG. 2. Various channels are described and referenced, however it is to be understood that the channels are referred to according to their function, and, as is shown, several are contiguous. In general, microfluidic chip 200 contains inlets (or outlets) and channels, and/or chambers. Inlets/outlets allow access to the different reservoirs to which they are connected for the purpose of introducing or removing fluids from the channels/chambers on the microfluidic chip 200. A contiguous fluid path through the inlet allows the passage of electrical current through conductive fluids. It will be understood that the number of inlets/outlets, channels/chambers, their size and configuration, placement, or other design or geometrical arrangement will vary according to the application contemplated on the microfluidic chip. In some embodiments, the configuration of the microfluidic chip will vary according to the physics and chemistry used to perform a microfluidic separation based on a particular analyte characteristic including, but not limited to, electrophoretic mobility, molecular weight, hydrodynamic volume, isoelectric point, or partition coefficient.

FIG. 2 depicts one embodiment of a configuration of a microfluidic chip for use in embodiments of the present invention. The microfluidic chip shown in FIG. 2 is exemplary only, and is not intended to limit the invention to use of the chip shown in FIG. 2 or the separation procedure described with reference to FIG. 2. The microfluidic chip 200 contains a separation channel 202 that allows the needed residence time for samples traversing the separation channel time to divide into distinct zones. The head of the separation channel 202 is connected to the tail of an injection cross 204. The sample to be separated is shuttled into the injection cross 204 defining a physical plug of material to be separated on the separation channel 202. The other end of the separation channel is connected to a waste channel 206, which is connected to the waste inlet 207. A buffer waste reservoir, or waste reservoir, is in fluidic communication with the waste inlet 207 of the microfluidic chip through a needle. An electrode, connected to a power module, in the waste reservoir provides voltage and current to the waste inlet 207 for moving fluids into and away from the injection cross 204 through the waste channel 206 and the separation channel 202. Additionally the waste reservoir accepts separated sample zones that pass through the separation channel 202 into the waste channel 206 and waste inlet. In one embodiment, the waste reservoir serves as a sink for separation media from separations involving electroosmotic flow. Under the influence of an electric field, electroosmosis pushes fluid into the waste reservoir from the separation channel through the waste channel, the waste inlet and the waste port. The fluid in the waste reservoir is designed to resist changes in pH caused by the flow of electric current through the waste reservoir fluid, waste channel and separation channel. In one embodiment, once the waste reservoir is full, or the pH of the fluid in the waste reservoir has changed a predetermined amount, the waste reservoir is manually removed from the reservoir module, reset and returned to the reservoir module. This process could be automated similar to the sample reservoir, described below.

The head of the injection cross 204 is connected to the buffer channel 208, which is connected to the buffer inlet 210. The buffer inlet 210 is in fluid communication with a buffer reservoir in the reservoir module through a needle. An electrode, connected to a power module, in the buffer reservoir provides voltage and current to the buffer inlet 210 for moving fluids into and away from the injection cross 204 through the buffer channel 208. In one embodiment, the buffer reservoir serves as a source of separation media for separations involving electroosmotic flow as a fluid flow component of the separation. Under the influence of an electric field, electroosmosis draws fluid from the buffer reservoir into the separation channel 202 through the buffer channel 208 and buffer inlet 210. The fluid in the buffer reservoir is designed to resist changes in pH caused by the flow of electric current through the buffer reservoir fluid and the buffer channel 208, in one embodiment. In one embodiment, once the buffer reservoir is empty, or the pH of the fluid in the buffer reservoir has changed a predetermined amount, the buffer reservoir is manually removed from the reservoir module, reset and returned to the reservoir module. This process could be automated similar to the sample reservoir, described below.

The string of buffer channel, injection cross, separation channel and waste channel define a contiguous fluid element for separation of a sample. The voltage and current from the electrodes in contact with fluids entering the buffer inlet and the waste inlet dominate the separation portion of the analysis, as known in the art.

A sample loop channel 212 is provided for accepting and storing sample that is introduced onto the chip through the introduction port and entering injection inlet 214. One end of the sample loop 212 connects with the injection inlet 214, the other with the sample inlet 216. The sample inlet 216 is in fluid communication with a sample reservoir in the reservoir module. An electrode, connected to a power module, in the sample reservoir, described above, provides voltage and current to the sample inlet for moving fluids into and away from the injection cross 204.

The sample channel 218 connects the sample loop channel 212 with one end of the injection cross 204. The sample reservoir, in fluid communication with the sample inlet 216 through a needle, accepts fluid that is flushed through the sample loop channel 212. In one embodiment, subsequent pressurized injections of sample into the sample loop channel 212 force fluid previously contained in the sample loop channel 212 into the sample reservoir through the sample inlet 216. In one embodiment, once the sample reservoir is filled, the sample reservoir is manually removed from the reservoir module, and optionally reset and returned to the reservoir module. This process could be automated with a sensor inside the reservoir to detect the fluid level and to activate or deactivate a pump to remove fluid from the reservoir at set fluid levels, in some embodiments.

The sample waste channel 220 connects to the injection cross 204 end opposite the sample channel 218. The sample waste channel 220 connects to the sample waste inlet 222 which is in fluid communication with a sample waste reservoir through a needle. An electrode, connected to a power module, in the sample reservoir provides voltage and/or current to the sample waste inlet 222 for moving fluids into and away from the injection cross 204 through the sample waste channel 220. Additionally, the sample waste reservoir accepts fluid that is flushed through the sample waste channel 220. In one embodiment, fluid from the sample channel 218 that is flushed through the injection cross 204 into the sample waste channel 220 is eventually passed through the sample waste inlet 222 into the sample waste reservoir. In one embodiment, once the sample waste reservoir is full, the sample waste reservoir is manually or automatically, for example with a robotic system, removed from the reservoir module, reset and returned to the reservoir module. This process could be automated similar to the sample reservoir.

The string of sample loop channel 212, sample channel 218, injection cross 204, and sample waste channel 220 define a contiguous fluid element for electrokinetic injection of the sample. The voltage and current from the electrodes in contact with fluids entering the sample inlet and the sample waste inlet dominate the electrokinetic injection of the sample, as known in the art.

In the preferred embodiment, the sample waste reservoir, buffer reservoir and waste reservoir contain the same fluid that is used for the separation medium. Once full, the reservoirs are emptied into a combined waste reservoir that may be contained either integral to or separate from the reservoir module.

Various mechanisms may be employed in embodiments of the invention to manipulate, transport, and/or move fluid within the microfluidic chip, as well as into or out of the chip. In some embodiments, pressurized fluid flow is applied from a syringe, or other pressure source, attached to a port. For example, in one embodiment, fluid is driven by a syringe into a flush channel, and thereby into all channels of microfluidic chip 200 in FIG. 2 during separation media filling or exchange. In some embodiments, pressurized injection of a sample occurs into the sample loop 212. In some embodiments, hydrostatic flow is generated by unequal fluid heights in reservoirs in fluidic communication with the microfluidic chip 200. In some embodiments, electroosmotic flow is generated by application of a voltage to surface charged microfluidic channels containing a conductive solution.

In some embodiments, a pressure stop is positioned between two or more channels in a microfluidic chip. For example, in some embodiments, a stop is positioned between the sample loop 212 and the sample channel 218, referring to FIG. 2. The sample loop is deeper than the sample channel. A first pressure is required to inject fluid into the sample loop. This pressure is not large enough, however, to force fluid into the sample channel. Accordingly, the sample channel (and other connected channels) are pressure-isolated from the pressure injection.

In some embodiments, a filter is positioned in a microchannel on the microfluidic chip to prevent the passage of certain particles, or other analytes. The filter is constructed, in one embodiment, by introducing a wide and shallow section of a channel between two deeper sections of channel. For example, a filter may be placed in the flush channel, referring to FIG. 2, in between the flush inlet and the buffer channel. In this manner, the injection cross and separation channel would be protected from particles in the flush fluid.

Other pumps, valves, and mixers known in the art may find use in embodiments of the present invention to manipulate or transport fluid, as appropriate.

Microfluidic chips of the present invention may be fabricated using a variety of techniques, including, but not limited to, hot embossing, such as described in H. Becker, et al., Sensors and Materials, 11, 297, (1999), hereby incorporated by reference, molding of elastomers, such as described in D.C. Duffy, et. al., Anal. Chem., 70, 4974, (1998), hereby incorporated by reference, injection molding, LIGA, soft lithography, silicon fabrication and related thin film processing techniques, as known in the art. In a preferred embodiment, glass etching and diffusion bonding of fused silica substrates are used to prepare microfluidic chips.

A detection module, or 'detector module' as used herein, is provided to detect the presence of a target analyte in a portion of the separation channel. In some embodiments, components complementary to those of the detection module are included on the microfluidic chip and/or reservoir. For example, in some embodiments, electrodes for performing electrochemical detection are formed on the interior and exterior surfaces of the microfluidic chip and are in electrical communication with the separation channel and the detector. For example, in some embodiments, additional channels and reservoirs are included in the reservoir module to add reagents to the separation channel for chemiluminescence detection. In some embodiments the method of detecting the presence of target analytes in the separation channel includes, but is not limited to, optical absorbance, refractive index, fluorescence, phosphorescence, chemiluminescence, electrochemiluminescence, electrochemical detection, voltammetry or conductivity. In preferred embodiments, detection occurs using fluorescence and more preferably, laser-induced fluorescence, as is known in the art.

Generally, optical detection of non-fluorescent target analytes involves providing a colored or luminescent dye as a 'label' on the target analyte. Fluorescent analytes may be directly detected by optical methods described below. Preferred labels include, but are not limited to, fluorescent lanthanide complexes, including those of Europium and Terbium, fluorescein, fluorescamine, rhodamine, tetramethylrhodamine, eosin, erythrosin, coumarin, methyl-coumarins, pyrene, Malacite green, stilbene, Lucifer Yellow, Cascade Blue™, Texas Red, 1,1'-[1,3-propanediylbis[(dim-ethylimino-3,1-propanediyl]]bis[4-[(3-methyl-2(3H)-benzoxazolylidene)methyl]]-,tetraioide, which is sold under the name YOYO-1, Cy and Alexa dyes, and others described in the 9th Edition of the Molecular Probes Handbook by Richard P. Haugland, hereby expressly incorporated by reference. Labels may be added to 'label' the target analyte prior to introduction into the microfluidic chip, in some embodiments, and in some embodiments the label is added to the target analyte in the microfluidic chip. In general the labels are attached covalently as is known in the art, although non-covalent attachments may also be used.

Further, as is known in the art, photodiodes, confocal microscopes, CCD cameras, or photomultiplier tubes maybe used to image the radiation emitted by fluorescent labels.

In a preferred embodiment, detection occurs using laser-induced fluorescence, as known in the art. Accordingly, in some embodiments, the detector module includes a light source, detector, and other optical components to direct light onto the microfluidic chip and collect fluorescent radiation from the target analyte. The light source preferably includes a laser light source, more preferably a laser diode, and still more preferably a violet or a red laser diode. A violet, or blue, laser diode is preferred in embodiments of the present invention to detect a fluorescamine label on one or more components of the sample. A fluorescamine label is preferred, in embodiments of the present invention, because the fluorescamine label attaches quickly (in milliseconds, in some embodiments) to the components of interest. Accordingly, fluorescamine is preferred in some embodiments to facilitate faster detection of one or more sample components. Violet, or blue, optical sources are accordingly preferred to excite the fluorescamine label. Other color laser diodes may be used, including red laser diodes, as well as other light sources including, but not limited to, laser diodes, light-emitting diodes, VCSELs, VECSELs, and diode-pumped solid state lasers. In some embodiments, a Brewster's angle laser induced fluorescence detector is used. One or more beam steering mirrors are used, in one embodiment, to direct the beam to a detection area on the microfluidic chip. In preferred embodiments, the beam is directed onto the microfluidic chip at Brewster's angle for the material of the chip. For example, in preferred embodiments the microfluidic chip comprises fused silica and the laser diode is directed onto the microfluidic chip at Brewster's angle for fused silica. Beam conditioning optics—including any of, but not limited to lenses, filters, and/or pinholes—may be used to focus the beam onto the microfluidic device. Dye may be injected into the microfluidic chip, in one embodiment, to visualize the location of the beam. A lens is used to collect and collimate the fluorescence and scattered light from the fluidic device. In embodiments where the microfluidic chip comprises a plurality of microchannels, each having a detection area, the detector module comprises a plurality of laser diodes (or other light sources), a plurality of beam steering mirrors to direct light from each diode to a microchannel. The collected light passes through a filter to remove the scattered laser light and the balance of the emissions are detected with a single photomultiplier tube for all channels. To eliminate cross-talk between the detection of each channel, electronics are used to alternately pulse each of the diode lasers so that fluorescence is only generated on one of the fluidic channels at any one time. In a preferred embodiment, the microfluidic chip includes 2 microchannels, and the detector comprises 2 laser diodes. However, any number of microchannels and laser diodes may be used, including, for example, 1, 2, 3, 4, 5, 6, 7, 8, 9, or 10 microchannels and a corresponding number of laser diodes.

In a preferred embodiment, the detector module comprises a laser-induced fluorescence photometer, an example of which is shown in FIG. 3. In these embodiments, a collinear, or epifluoresence, optical configuration is used to deliver a focused beam of light to a microfluidic chip and collect and detect the fluorescence generated. In these embodiments, the detection module 300 includes a light source 302, as described above. The light source is placed into a variable x-y mount, in some embodiments, to facilitate alignment of the illumination with the separation channel. The laser light source may be collimated using collimating objective 304, most preferably an aspherical lens, and passed through an excitation filter 305 to reject laser diode emissions outside the desired wavelength range. The collimated beam is reflected off a plurality of reflectors 306, with 4 dichroic reflectors being particularly preferred, to further condition the laser beam before passing into a beam steering block 309. The collimated beam is reflected off a dichroic reflector 308 and focused on the microfluidic chip with an objective 310. The same objective 310 collects the emissions from the microfluidic chip and the collimated emissions are passed through the dichroic folding mirror 308. Emissions are reflected off mirror 312, pass through emission filter 313, which rejects light that is not from fluorescence, in some embodiments. Fluorescence emissions impinge on a photodetector 314 and result in an electrical response, as known in the art.

The laser is aligned to the chip by translating the beam steering block back and forth across the microchannel. In a preferred embodiment, the laser is aligned by adjusting an adjustor coupled to the detection module. The adjustor may be any mechanical means capable of moving the laser light source on the mount—a screw, knob, button, motor, pulley, slide, or other manipulation means known in the art. In some embodiments, the reservoir module defines the position of the detection window to the microfluidic chip spatially with respect to the cover of the detection module. The beam positioning block translates the objective lens, and thus the focal spot of the laser with respect to the detection window, via the adjustor. In some embodiments, the location of the focal spot with respect to the detection region of the channel can be viewed above the reservoir module on a screen by observing the interference pattern created as the light passes through the microfluidic channel. In some embodiments, the alignment of the light source to the separation channel is visually accomplished by means of an optical viewing apparatus such as a telescope, microscope, display, and the like. The lens position is adjusted until the center of the interference pattern is visualized on the screen. In one embodiment, the adjustment of the lens is done manually and the instrument operator performs the visualization of the interference pattern. This process could be automated such as described in Patent Application Number 2003/0127610, "Methods and Systems for Alignment of Detection Optics". Accordingly, alignment of the light source, in some embodiments of the present invention can be manually performed in under 10 minutes, in some embodiments under 5 minutes, in some embodiments under 1 minute, and in a preferred embodiment a laser light source can be aligned to the detection area in about 30 seconds.

A detection module suitable for use with embodiments of the present invention is further described in U.S. patent application Ser. No. 10/633,794 entitled "Optical Detector System", filed 4 Aug. 2003.

A power module is included in embodiments of the present invention to provide the voltage and/or current necessary to operate the remaining modules—such as pumps and/or valves on the microfluidic chip and the detector module. In some embodiments, the power module includes a high voltage power supply including a DC-to-DC convertor, a voltage-controlled resistor, and a feedback circuit to control the resistor and converter to regulate the voltage of the high voltage supply. By 'high voltage' herein is meant voltage sufficient to allow electrokinetic pumping of fluid, as described above. Thus, 'high voltages' generally refer to voltages above 100V. Generally, high voltages up to 500 V may be provided, more preferably 800 V, still more preferably 1,000 V, yet more preferably 5,000 V, and still yet more preferably 10,000 V. Embodiments of a power module suitable for use in the present invention are described in U.S. application Ser. No. 10/414,979 entitled "Modular High Voltage Power Supply for Chemical Analysis", filed 16 Apr. 2003 and U.S. patent application Ser. No. 10/454,179 entitled "Scalable Power Supply", filed Jun. 3, 2003, both of which are hereby incorporated by reference.

In embodiments of the present invention, the power module is coupled to an external power supply. In other embodiments, the power module is powered using a portable power supply, such as batteries, solar power, wind power, nuclear power, and the like. Accordingly, in embodiments of the present invention, the power module operates using less than 3V of DC power. In a preferred embodiment, 6 V of DC power are used to power the portable device.

The power module is coupled to the electrodes in one or more reservoirs. In some embodiments, the power module is coupled to electrodes located on or in the microfluidic chip. In one embodiment, The power module is coupled to the electrodes in contact with the reservoirs by way of an electrode plate containing interconnects in electronic communication with the electrodes in the reservoirs and a wire or other electrical connection to the power module. In this manner, the power module itself can be disconnected from the reservoir module and/or microfluidic chip and be changed, such that a different voltage may be provided or the module simply replaced. In some embodiments, the power module is operated in constant current mode wherein the power module provides a constant output of current by varying the voltage applied by the power module to the fluid, and therefore the microfluidic channel. In some embodiments, the power module is operated in constant voltage mode wherein the power module provides a constant voltage potential to the microfluidic channel and allows the current to vary according to the conductivity of the microfluidic channel. Constant current mode generally maintains a constant electric field between the electrodes and is generally preferred, as migration times, without being bound by theory, are generally more repeatable and reliable.

In further embodiments of the present invention, one or more processor modules are provided in communication with the detection module and power module to collect and/or analyze data generated by the system. In some embodiments of the present invention, a user interface is coupled to a processor module. The user interface may include a visual display, for example, in one embodiment an LCD display, a keypad, one or more buttons, a mouse, and/or the like. In some embodiments, the user interface is menu-driven. The user interface allows a user, in some embodiments, to view data, to select the detection technique, to determine which separation channel to use, to determine which of a plurality of detection modules to activate, and the like.

In preferred embodiments of the present invention, at least one reservoir module, a microfluidic chip, a power module, and a detector module are interconnected as generally described above and packaged within a single housing. In some embodiments, a plurality of microfluidic chips are provided within a single housing along with a plurality of power modules and a plurality of reservoir modules and detector modules. The individual modules can be replaced without removing or exchanging the remaining modules. Dovetail rails and other mechanical assemblies facilitate the swapping of modules in and out, in some embodiments. In some embodiments the housing containing the modules further comprises heat sinking and/or ventilation, as known in the art, to maintain the various modules at or near ambient temperature. In some cases, heating and/or cooling elements may also be provided. The housing containing the modules is desirably rugged and portable, in preferred embodiments.

Methods for detecting a target analyte in a sample according to embodiments of the present invention generally proceed as follows. A sample is brought into contact with a sample introduction port. In some embodiments, the sample is injected through the housing in which the reservoir module is placed. That is, a sample introduction port is provided in the housing in fluid communication with the sample introduction port in the reservoir module. In some embodiments, no external housing is present. A sample is injected into the sample introduction port of a reservoir module filling the injection inlet, sample loop channel and sample inlet of the microfluidic chip. Excess sample moves through the sample inlet, through a needle and into a sample waste reservoir.

One or more channels in the microfluidic device may be flushed. A syringe containing separation media is connected to a channel flush port in the reservoir module. Separation medium is pushed into the reservoir module entering the microfluidic chip at the flush inlet, filling all channels/chambers and exiting the chip inlets. Optionally, separation medium is also injected into the sample loop channel with a syringe through the introduction port in some embodiments.

A microfluidic separation is performed, as known in the art. The particular procedure for performing a microfluidic separation will vary according to the type of separation performed and the microfluidic chip configuration. In one embodiment, the separation proceeds as follows, with reference to FIG. 2, a voltage and current are applied to the sample electrode and sample waste electrode positioned in the sample reservoir and sample waste reservoir, respectively. Referring back to FIG. 2, sample in the sample loop channel moves under the influence of the electric field and fills the sample channel, injection cross and begins to fill the sample waste channel. In one embodiment, a smaller voltage and current is applied to the buffer electrode and waste electrode, positioned in the buffer reservoir and waste reservoir, respectively, to help confine sample in the injection cross; a pinched injection as is known by those familiar with the art. The voltages and currents causing the electrokinetic injection are turned off. A voltage and current are applied to the buffer electrode and waste electrode, positioned in the buffer reservoir and waste reservoir, respectively, in one embodiment. The sample contained in the injection cross moves into the separation channel and begins to divide into individual analyte zones. In one embodiment, a smaller voltage and current are applied to the sample electrode and sample waste electrode to prevent sample from spilling from the sample channel and sample waste channel into the injection cross and the separation channel; also known as an anti-siphoning voltage by those familiar with the art. The separation voltage is applied until the individual analyte zones pass through the separation channel, past the detection area and into the waste channel. The time between the application of the separation voltage and the appearance of the center of the analyte zone in the detector signal defines the time for the analyte in the sample, in one embodiment, and is indicative of the presence of the analyte in the sample. Time may be converted into a characteristic for the component, such as electrophoretic mobility, molecular weight, hydrodynamic volume, isoelectric point, or partition coefficient, in some embodiments to facilitate determination of the component and/or analyte. The analysis process may be repeated by injection of a second sample into the sample loop channel, in some embodiments.

Accordingly, an elution spectrum is generated according to the particular separation technique used. The elution spectrum generally contains a plurality of peaks, each indicating a migration time of one or more sample components. The migration time is indicative of a separation characteristic, as determined by the separation technique used. Separation characteristics include, for example, the component characteristics described above. One or more calibrations may also be performed, as generally known in the art.

At least one component of the separated sample is detected. Generally, a 'component' of the sample may be any of the target analytes described above. Some target analytes, however, will include several separated 'components', such as viruses (which, for example, include a plurality of proteins). The component may be directly detected—for example, by tagging the component with a fluorescent label. In some embodiments, a substance indicative of the presence of a component or target analyte may be detected—for example, using an eTag™ reporter (ACLARA Biosciences™; Mountain View, Calif.). Based on the detected component, or in some embodiments, based on the detection of a plurality of components, the target analyte is identified. The identification generally proceeds by correlating the signal generated by the detection module with a signal for a known target analyte, or of components of interest. In some embodiments, if a correlation cannot be made between the signal generated by the detection module and a signal for known target analytes, the presence of an analyte is reported, but its identity remains unknown.

Further in some embodiments, the quantity of target analyte in the sample is also reported. The quantity of analyte is determined by comparing the signal generated by the detection module with a calibration curve for the analyte of interest.

The presence of the target is then indicated on an output interface of the portable device. The indication may include, but is not limited to, a visual display, an audible sound, a tactile signal, or any combination thereof.

In embodiments where a plurality of microchannels are provided on a microfluidic chip, a second portion of the sample fluid may be transported to a second separation channel, and a detection area on the second separation channel is interrogated with the detection module. In some embodiments, a plurality of microfluidic chips is provided, each with one or more separation channels. A single sample may be injected and multiplexed onto each chip, in one embodiment. In another embodiment, separate samples, or portions of a single sample, are injected, one into each microfluidic chip. In some embodiments where a plurality of microfluidic chips are provided, one or more microfluidic chips are configured to perform the same or different microfluidic separation method and, where one or more samples are introduced into the device, the distribution of samples among microfluidic separation methods can be in any association.

The detector module, power module, reservoir module and/or microfluidic chip can be removed from the system and replaced, or a second module inserted. Changing detector modules, for example, allows for a change in light source, wavelength, or light intensity from one separation measurement to the next or changing from one detection method to another. Change microfluidic chips allows for a change in the application of the system. Changing power sources provides a change in voltage and/or power level.

EXAMPLES

Example 1

Microfluidic Chip Fabrication

The microchip was fabricated from Corning 7980 fused silica wafers (100 mm diameter, 0.75 mm thickness using standard photolithography, wet etch, and bonding techniques. Fused Silica wafers were PECVD deposited with amorphous silicon (150 nm), which served as the hard mask. A 7.5-micron thick layer of positive photoresist was spin-coated and soft-baked (90 C, 5 minutes). The mask pattern was transferred to the photoresist by exposing it to UV light in a contact mask aligner. After exposure, the photoresist was developed and hard-baked (125 C, 30 minutes). Exposed silicon was etched in a plasma etch tool. Silicon etch process consisted of a 30 second oxygen ash @ 200 W DC & 25 mTorr, followed by 150 second SF6 @ 200 W DC & 50 mTorr. The subsequently exposed glass was etched with a 49% HF solution. Via access holes were drilled in the cover plate (Corning 7980) with diamond-tipped drill bits. The etched wafers and drilled cover plates were cleaned with 4:1 H2SO4:H2O2 (100 C), de-stressed with 1% HF solution, then the surfaces were treated in 80 C 40% NaOH, rinsed in a cascade bath, followed by a spin rinse dry, aligned for contacting, and thermally bonded at 1150 C for 5 hours in an N2-purged programmable muffle furnace. The standard chips were cut with a programmable dicing saw containing a diamond composite blade into 25.4×25.4 mm or 20×20 mm devices depending upon design.

Example 2

A portable, modular analysis device

FIG. 4 shows an exploded view of an embodiment of the device, indicated generally at 10. Externally, the device is comprised of a top (or cover) plate 11, a case or shell 12, and a back cover 13—together, a housing. In the embodiment illustrated here, top plate 11 incorporates a 4-button menu-driven interface 14 and lighted LCD screen 15 for programming separation conditions and for presenting analytical results, a serial port computer connection 16 and 6-volt electrical connection 18 for use when wall power is available.

FIG. 5 is a view of the underside of cover plate 11 showing the general arrangement of an embodiment of a power module on a high voltage board carrier 21. The power module comprises a plurality of high voltage boards 22 that provide the electric field required to drive the chemical separations and manipulate fluid samples for such operations as sample loading in each microchannel. In this embodiment, the high voltage board carrier is designed to accommodate up to 12 high voltage boards corresponding to 6 boards per separation channel.

The high voltage boards are each capable of delivering up to +/−5 kV at less than 100 µA and are designed to survive repeated direct shorts to ground such as might result from fluid leaks or device mishandling. They also feature an electronically controlled potential float, bi-directional current capability, real time current monitoring, and current source-or-sink capability. The modularity of the high voltage boards provides for their easy replacement, exchange, or addition depending on the configuration needed to provide for desired system function. Connection between the high voltage boards and separation module 42, for which they supply the requisite electric fields, is by means of electrical cable 25 connected to electrode plate 45. A more complete discussion of the features of these novel high voltage boards can be found in U.S. patent application Ser. No. 10/414,979 filed Apr. 16, 2003 and entitled "Modular High Voltage Power Supply for Chemical Analysis", incorporated herein in its entirety.

A main control board 27 provides the requisite electronics for all subsystem control, including user interface, data acquisition, and data reduction.

FIG. 6 is a view of the rear of device 10 showing back cover 13 and introduction ports 32 for pressure injecting samples into a means for receiving a liquid sample for subsequent analysis. Latches 35 provide access to the inside of the device. When the latches are opened the back plate can be removed for access to analysis modules 42. One embodiment of the device includes two adjacent but independent analysis modules 42 (FIG. 7). The analysis modules are positioned on case 12 by a dovetail rail arrangement. Each analysis module has a male dovetail rail 47 mounted to its underside and is supported by a vibrationally isolated female dovetail rail (not shown) within and attached to case 12. Thus, each analysis module can be easily and independently removed and replaced by sliding the module along the mating rails after first disconnecting electrode plate 45 and electrical cable 25. A ball detent (not shown) holds each analysis module in place until the back plate is reinstalled.

The analysis module comprises, in combination, a separation module in fluid communication with a detector module. Referring now to FIGS. 7 and 8, which show separation module 52 superposed onto detector module 55 to form the unitary analysis module 42. Electrode plate 45, attached to separation module 52, provides connection between high voltage boards 22 and separation module 52. The separation module and detection module are each totally self-contained and separable such that one or the other can be replaced without affecting operation of the remaining module or the device itself.

The components of separation module 52 are shown in an exploded view in FIG. 9. The separation module is comprised of a stacked arrangement of components that includes, in serial order; electrode plate 45, connecting fluid reservoirs 65 to high voltage boards 22, attached to top cartridge housing 62, reservoir base 68, that supports a plurality of individual, contiguous fluid reservoirs 65 that hold the fluids required for sample analysis, fluid manifold base 67 that holds the plurality of reservoirs, and microfluidic chip 63 sealed to the bottom of the fluid manifold with O-ring seals by means of compression plate 64 and compression frame 66. Alignment pins 69 are provided to maintain alignment of the components of cartridge housing 62.

FIG. 10 is a cross-sectional view of one embodiment of a fluid reservoir structure. In this embodiment the fluid reservoir 65 is provided with a concentric electrode 72, in contact with electrode plate 45, and a septum flange 77 holding a septum 78 that provides for fluid communication with capillary interconnect devices 66.

In addition to holding the plurality of reservoirs, fluid manifold 67 also contains capillary interconnect devices 66. These devices provide both for transporting fluid from the fluid reservoirs as well as electrical contact to microfluidic chip 63 where chemical separation takes place within one or more microchannels that can be etched, machined or molded into the microfluidic chip. The design and construction of capillary interconnect devices such as 66 is disclosed in U.S. patent application Ser. No. 10/350,541, "Capillary Interconnect Device" filed Jan. 24, 2003 and U.S. patent application Ser. No. 10/405,204, "High Pressure capillary Connector" filed Apr. 2, 2003, incorporated by reference herein in their entirety.

A microfluidic chip provides for capillary chromatographic separation of a liquid sample into its chemical components. Microfluidic chip 63, such as that shown in FIG. 10, typically consists of one or more grooves, or microchannels, and chambers that define separation channel 75. The separation channel can be etched, molded or machined into the surface of a substrate that can be silicon, quartz, glass, or a polymer material. The size, shape and complexity of these microchannels and their interconnections influence the limits of the microfluidic chip's functionality and capability to separate the components of a liquid sample. In turn, the size, shape and complexity of microchannels and structures that can be used in microfluidic systems depend on the materials used and the fabrication processes available for those materials. The typical overall channel sizes range from about 5-100 µm wide and 5-100 µm deep. Multiple channel depths are provided to isolate pressure differentials that can exist between different channels. Included within the structure of the microfluidic chip are spaced electrodes 72 for producing an electric field in the microchannels.

In order to improve the resolution of the separation channel, i.e., separation of chemically similar components of the sample introduced onto the separation channel, it is desirable to make the channel as long as reasonably possible. On the other hand, the separation channel must also fit within the confines of the microfluidic chip itself. In the illustrated embodiment, microfluidic chip 63 is square in shape and about 2 cm long on each side. Separation channel 75 is etched into the surface of the chip in a serpentine pattern to accommodate the entire 10 cm length of the channel. Other channel configurations are also contemplated such as those disclosed in U.S. Pat. No. 6,270,641 "Method and Apparatus for Reducing Sample Dispersion in Turns and Junctions of Microchannel Systems" issued Aug. 7, 2001 and U.S. patent application Ser. No. 10/039,938 "Compact Microchannel System" filed Oct. 19, 2001 incorporated herein in their entirety. Additionally, resolution of the separation process can be improved by controlled transport through a junction as disclosed in U.S. patent application Ser. No. 09/714,410 "Method and Apparatus for Sample Injection in Microchannel Devices", filed Nov. 14, 2000 incorporated herein in its entirety.

Referring now to FIG. 9, which illustrates the analysis scheme used by the device, generally, a sample to be analyzed is injected into a receiving means that can include introduction port 32 and at least one of reservoirs 65, here sample reservoir 65a. A portion of the injected sample is drawn into the flow channel 74 leading from the sample reservoir 65a to waste, reservoir 65b by application of a voltage between electrode 72a, contained within sample reservoir 65a and electrode 72b contained within sample waste reservoir 65b. As a result of this operation, a portion of the sample flowing in channel 74 between the sample and sample waste reservoirs resides in the Z-bend in channel 74 (FIG. 12 inset). This portion forms an injection plug which is subsequently injected into separation channel 75 by application of a voltage between electrode 72c contained within buffer reservoir 65c and electrode 72d contained within waste reservoir 65d. The volume of the injected is determined by the dimensions of the Z-bend.

As the sample moves through the separation channel components of the sample are separated based on their chemical and/or physical properties. At the end of the channel, the separated components of the sample pass through detection window 76 and in this embodiment are detected by laser-induced fluorescence. For those materials that do not fluoresce naturally it has been found to be particularly convenient to tag the components of the sample with a fluorescent dye responsive to energetic radiation, such as from a laser. Microfabricated in-line filters can be incorporated into each end of the separation channel for particle exclusion. Table 1 shows a voltage scheme that can be used for the injection and separation operations described above.

TABLE 1

| Channel | Injection (V) | Separation (V) |
|---|---|---|
| Sample | 0 | 450 |
| Sample Waste | 900 | 450 |
| Buffer | 400 (0.6 µA) | 0 |
| Waste | 450 | 4500 (11 µA) |

FIG. 11a is a view of the detector module, indicated generally at 55, which is positioned directly beneath separation module 52 (cf. FIG. 8). In the illustrated embodiment, the optical detector system is comprised generally of two modules, optics module (B) that contains the light source and associated optical elements for generating, collimating, shaping the light beam, directing the resulting light beam onto a detection region, and collecting the resulting fluorescent radiation. Detector module (C) contains detection means for receiving and analyzing the emitted radiation. Optics module B is in optical communication with detector module C and, as illustrated in FIG. 11a, can be superposed onto module C. In the configuration illustrated in FIG. 11a, the light source and associated optical means are combined with detection means into a unitary structure that provides for isolating stray light arising from the excitation source from the detector. Moreover, the totally enclosed package excludes room light. The terms "light" and "radiation" are used herein interchangeably and synonymously.

External detector module features such as alignment pins 85 for correctly positioning the microchip detection window 76 over the radiation beam, objective lens 87, detector cover 82, and laser/photomultiplier board 83 are shown in FIG. 11a.

Removing detector cover 82 shows the optical components of the detector module (FIG. 11b), including light source 86, that can be a generic light source. Potential light sources include, but are not limited to light-emitting diodes, laser diodes, vertical cavity surface emitting lasers (VCSELs), vertical external cavity surface emitting lasers (VECSELs), dipole pumped solid state (DPSS) lasers or fiber optic connections that are subsequently coupled to light sources such as large laser systems, laser diodes or lamps. In the embodiment shown in FIG. 11b, the light source is a laser and preferably a laser capable of generating light having a wavelength of about 405 nm.

In keeping with an object of the invention, the ability to replace components without the necessity of realignment or recalibration, the light source and associated collimating optics and filters are combined together in an aligned dovetail rail assembly, indicated generally at 88 in FIG. 11b. This combination is a unitary structure that comprises light source 86 and associated collimating optics 89 and filters 97 in a stable, fixed relationship with one another, demountably engaged with dovetail rail 95. Not only does this unique feature provide for easy replacement of the light source and/or associated optical components but also ensures that established alignment will be maintained if the rail assembly or any of its components are replaced.

The collimated beam from light source 86 is reflected off dichroic reflectors or mirrors 82, to reject some broadband emissions. In the embodiment illustrated in FIG. 11b a four-mirror configuration used. This mirror configuration is especially advantageous in that it is simple to align the laser beam (eliminating the use of conventional pinholes) and provides a long optical path (4.5 to 5 inches) so that the laser beam can be conditioned properly, both spatially and spectrally. Because of space requirements, the novel folded path is used for coupling to the light source, thereby accommodating the desirable long optical path.

The conditioned light beam is focused onto the detection region 76 that can be the detection region of an associated microfluidic chip or chromatographic column with aspherical objective lens 87. This same lens is used to collect fluorescence emitted by the constituents of the sample in detection region 76. The collimated fluorescent radiation emitted by the sample is passed through a dichroic filter and into detector module C of optical detector system where it can be directed onto radiation detection means, such as a photon detector.

In the embodiment illustrated here, photon sensing is by a photomultiplier tube (PMT). However, other photon sensing means are contemplated such as photodiodes, avalanche photodiodes or array detectors such as photodiode arrays and charge-coupled devices, or photon-sensitive detectors. These detectors can be run in either analog signal collection mode or photon counting mode.

An included microprocessor and software convert the signal provided by the photon detector into an elution spectrum. An analytical algorithm running on the embedded microprocessor compares the time-based elution spectrum characteristics to on-board databases, providing for agent identification and determination of concentration. The results can be displayed on screen 15.

A complete description of an optical detector system such as module 55, including the design and operation, is disclosed in U.S. patent application Ser. No. 10/633,794, "Optical Detector System" filed Jul. 15, 2003, incorporated herein in its entirety.

We claim:

1. A modular apparatus for detecting a target analyte, the apparatus comprising:
 a reservoir module comprising:
  a fluid manifold base defining a plurality of bays and a plurality of outlets, each outlet extending between one of the plurality of bays and a lower surface of the fluid manifold base; and
  a plurality of reservoirs coupled to the fluid manifold base positioned within one of the plurality of bays, wherein at least one reservoir comprises a reservoir seal and wherein at least one needle penetrates said reservoir seal;
 a microfluidic chip comprising:
  a planar upper surface and a planar lower surface, the planar upper surface abutting the lower surface of the fluid manifold base;
  a plurality of inlets piercing the upper surface, the inlets positioned in locations corresponding to the plurality of outlets of the fluid manifold base and each in fluid communication with one of the inlets,
   wherein said at least one needle is in fluidic communication with at least one inlet; and
  a separation channel embedded within the microfluidic chip between the upper and lower surfaces thereof the separation channel in fluid communication with at least one of said inlets;
  a sample introduction port embedded within the microfluidic chip between the upper and lower surfaces thereof, the sample introduction port in fluid communication with said reservoir module and at least one of the plurality of inlets;
  a seal positioned between the fluid manifold base and the microfluidic chip, the seal defining at least one area of fluidic communication between one of said plurality of outlets and one of said inlets;
  a detection module positioned to interrogate, at least a portion of the separation channel; and
 an output interface in communication with said detection module to indicate detection of the target analyte; and
 a power module for providing controlled current or voltage.

2. A modular apparatus according to claim 1, wherein the reservoirs are each coupled to the fluid manifold base with a fitting.

3. A modular apparatus for detecting a target analyte, the apparatus comprising:
 a reservoir module comprising:
  a fluid manifold base; and
  a plurality of reservoirs coupled to the fluid manifold base, wherein at least one reservoir comprises a reservoir seal and wherein at least one needle penetrates said reservoir seal;
 a microfluidic chip comprising:
  a plurality of inlets, wherein said at least one needle is in fluidic communication with at least one inlet; and
  a separation channel in fluid communication with at least one of said inlets
  a sample introduction port in fluid communication with said reservoir module and at least one of the plurality of inlets;
 a seal positioned between the fluid manifold base and the microfluidic chip, the seal defining at least one area of fluidic communication between one of said reservoirs and one of said inlets;
 a detection module positioned to interrogate at least one portion of the separation channel; and
 an outlet interface in communication with said detection module to indicate detection of the target analyte; and
 a power module for providing controlled current or voltage;
 wherein at least one of said plurality of reservoirs comprise at least two chambers, wherein one of the at least two chambers is in fluidic communication with at least one of said plurality of inlets, and the second of said at least two chambers is in electrical communication with the power module.

4. An apparatus according to claim 1, wherein each of said plurality of reservoirs further comprises an electrode, and wherein the power module is in communication with each of said electrodes.

5. An apparatus according to claim 4, wherein said power module is further in communication with said detection module.

6. An apparatus according to claim 1, wherein said microfluidic chip comprises a plurality of separation channels.

7. An apparatus according to claim 1, wherein said modular apparatus is portable.

8. An apparatus according to claim 1, wherein said modular apparatus is hand-held.

9. An apparatus according to claim 1, wherein the microfluidic chip, the reservoir module, the fluid manifold base, and the detection module are contained in a single housing.

10. An apparatus according to claim 1, wherein the detection module comprises a light source.

11. An apparatus according to claim 10, wherein the light source is a laser diode.

12. An apparatus according to claim 1, further comprising a plurality of microfluidic chips.

13. An apparatus according to claim 12, further comprising a plurality of fluid manifold bases.

14. An apparatus according to claim 12, wherein each of said microfluidic chips are configured to perform a different microfluidic separation.

15. An apparatus according to claim 1, further comprising a plurality of detection modules.

16. The modular apparatus of claim 1, further comprising a particulate filter incorporated within said sample introduction port.

17. The modular apparatus of claim 1, wherein said power module provides a source or a sink current.

18. A modular apparatus for detecting a target analyte, the apparatus comprising:

a reservoir module comprising:
- a fluid manifold base; and
- a plurality of reservoir coupled to the fluid manifold base, wherein at least one reservoir comprises a reservoir seal and wherein at least one needle penetrates said reservoir seal;

a microfluidic chip having upper and lower surfaces, the upper surface being in contact with the fluid manifold base, the microfluidic chip comprising:
- a plurality of inlets piercing the upper surface and positioned in correspondence with the plurality of reservoirs, wherein said at least one needle is in fluidic communication with at least one inlet; and
- a separation channel embedded within the microfluidic chip between the upper and lower surfaces, the separation channel being in fluid communication with at least one of said inlets; and a seal positioned between the fluid manifold base and the microfluidic chip, the seal defining at least one area of fluidic communication between one of said reservoirs and one of said inlets;

a detection module positioned to interrogate at least a portion of the separation channel; and an output interface in communication with said detection module to indicate detection of the target analyte; and a power module for providing controlled current or Voltage.

19. The modular apparatus of claim 18, wherein the separation channel has a circuitous shape and has a length substantially longer than a width thereof.

20. The modular apparatus of claim 19, wherein the separation channel has as a serpentine shape.

21. The modular apparatus of claim 18, wherein the power module is coupled to at least one of the reservoirs and the microfluidic chip to induce electroosmotic flow from the at least one reservoir into the microfluidic chip.

* * * * *